(12) United States Patent
Guillouzo

(10) Patent No.: US 9,765,300 B2
(45) Date of Patent: Sep. 19, 2017

(54) HEPATIC CELL LINES AND STEM-LIKE CELLS, METHODS OF MAKING AND USING THE SAME

(71) Applicant: Biopredic International, Saint-Grégoire (FR)

(72) Inventor: Christiane Guillouzo, Rennes (FR)

(73) Assignee: Biopredic International, Saint-Gregoire (FR)

( * ) Notice: Subject to any disclaimer, the term of this patent is extended or adjusted under 35 U.S.C. 154(b) by 0 days.

(21) Appl. No.: 14/717,700

(22) Filed: May 20, 2015

(65) Prior Publication Data

US 2016/0168536 A1 Jun. 16, 2016

Related U.S. Application Data

(60) Provisional application No. 62/090,191, filed on Dec. 10, 2014.

(51) Int. Cl.
*C12N 5/071* (2010.01)

(52) U.S. Cl.
CPC .......... *C12N 5/067* (2013.01); *C12N 2501/06* (2013.01); *C12N 2501/727* (2013.01); *C12N 2506/00* (2013.01); *C12N 2527/00* (2013.01)

(58) Field of Classification Search
CPC ................ C12N 5/067; C12N 2527/00; C12N 2506/00; C12N 2501/06; C12N 2501/727
See application file for complete search history.

(56) References Cited

U.S. PATENT DOCUMENTS

| 7,456,018 | B2 | 11/2008 | Gripon et al. |
| 2014/0273219 | A1 | 9/2014 | Jackson et al. |
| 2016/0168536 | A1 | 6/2016 | Guillouzo |

FOREIGN PATENT DOCUMENTS

EP 2671944 11/2013

OTHER PUBLICATIONS

Cerec et al. Transdifferentiation of Hepatocyte-Like Cells From the Human Hepatoma HepaRG Cell Line Through Bipotent Progenitor. Hepatology 2007;45:957-967.*
PCT/IB2016/000781 International Search Report dated Jul. 27, 2016.
Guguen-Guillouzo, et al., "Stem cell-derived hepatocytes and their use in toxicology," J. Toxicology, vol. 270, 2010, pp. 3-9.
Hart, et al., "A Comparison of Whole Genome Gene Expression Profiles of HepaRG Cells and HepG2 Cells to Primary Human Hepatocytes and Human Liver Tissues," The American Society for Pharmacology and Expérimental Therapeudcs, vol. 38, 2010, pp. 988-994.
He, et al., "5-azacytidine promotes terminal differentiation of hepatic progenitor cells," Molecular Medicine Reports, vol. 12, 2015, pp. 2872-2878.
Mann, et al., "Regulation of myofibroblast transdifferentiation by DNA methylation and MeCP2: implications for wound healing and fibrogenesis,"Cell Death and Differentiation, vol. 14, 2007, pp. 275-285.
Huangfu, et al., "Induction of pluripotent stem cells by defined factors is greatly improved by small-molecule compounds," Nature Biotechnology, vol. 26, issue 7, 2008, pp. 795-797.
Yamazaki, et al., "Sera from liver failure patients and a demethylating agent stimulate transdifferentiation of murine bone marrow cells into hepatocytes in coculture with nonparenchymal liver cells," Journal of Hepatology, vol. 39, 2003, pp. 17-23.
Guo, et al., "Similarities and Différences in the Expression of Drug-Metabolizing Enzymes between Human Hepatic Cell Lines and Primary Human Hepatocytes," Drug Metabolism and Disposition, vol. 39, 2011, pp. 528-538.

* cited by examiner

*Primary Examiner* — Taeyoon Kim
(74) *Attorney, Agent, or Firm* — Hovey Williams LLP

(57) ABSTRACT

New cell lines designated as Hepa-SC and Hepa-RP, originating from human hepatoma line HEPARG® are disclosed. Methods of inducing stemness in parental cells lines using mechano-transduction techniques, and redirecting stem-like cells to reprogrammed cells of a target differentiated population are also described.

8 Claims, 14 Drawing Sheets

HEPATIC CELL LINES AND STEM-LIKE CELLS, METHODS OF MAKING AND USING THE SAME

CROSS-REFERENCE TO RELATED APPLICATIONS

The present application claims the priority benefit of U.S. Provisional Patent Application Ser. No. 62/090,191, filed Dec. 10, 2014, entitled MECHANO-TRANSDUCED STEM CELLS AND METHODS OF MAKING AND USING THE SAME AND DERIVATIVES THEREOF, incorporated by reference in its entirety herein.

BACKGROUND OF THE INVENTION

Field of the Invention

The present invention relates to reprogrammed cells and stem-like cells of hepatic origin, and methods of making and using the same.

Description of Related Art

Some hepatoma cell lines have been extensively used such as HepG2, HuH7, etc. Such cells have drawbacks, including the lack of availability of a cell bank, and a progressive loss of many hepatic functions. HepaRG® cells (human hepatoma cell line deposit no. 1-2652, filed on 5 Apr. 2001 at the Collection Nationale de Cultures de Microorganismes, Institut Pasteur, 25 rue du Docteur Roux, F-75724 Paris Cedex 15, U.S. Pat. No. 7,456,018, incorporated by reference herein) are terminally differentiated hepatic cells derived from a human hepatic progenitor cell line that retains many characteristics of primary human hepatocytes. Cryopreserved and differentiated HEPARG® cells (Biopredic, Inc.) are now widely used for many cell-based applications. Up to now, this line has been the best hepatic cell line in its ability to morphologically and functionally mimic primary human hepatocytes in vitro.

One crucial advantage of HEPARG® is the established cell bank, making possible long term high level of functional stability by regularly restarting new batches of cells from the original pool of cells. However, HEPARG® has 3 main limitations: 1) The cell bank has some limitations in number of frozen vials, 2) Although the cells have high reproducibility for 17 passages, the stability of the line is limited to 17-18 passages, which represents a strong limitation for long term experiments (requiring delivery to customers at passage 12 for preserving the bank); and 3) The limited plasticity of the cells thus limiting diversification of properties and as consequence, also limiting new applications. There remains a need for hepatic cell lines with functions mimicking primary human hepatocytes.

SUMMARY OF THE INVENTION

The invention therefore aims to provide new HEPARG®-derived cell lines: 1—which could preserve their unique capacity to reach a level of differentiation such that these cells could express practically all of the functions of the normal human hepatocyte whilst actively proliferating; 2—which could solve the cell bank limitation; and 3—which could overcome the relatively short stability of HEPARG®.

Described herein is a stem-like cell line having the identifying characteristics of cells designated herein as Hepa-SC, which have been deposited at the Collection Nationale de Cultures de Microorganismes, Institut Pasteur, 25 Rue du Docteur Roux, F-75724 Paris, France, on May 19, 2015 under Deposit No. CNCM I-4980. Differentiated cells derived from the stem-like Hepa-SC cells are also described. Methods of producing stem-like cells from a parental cell line are also described. The methods general comprise culturing the parental cell line in the absence of a differentiation factor known for the parental cell line. The cultured parental cell line is subjected to mechanical stress to induce expression of stemness in the cells, which can be detected using known techniques. The stemness expression is then stabilized to yield the stem-like cells by exposing the cells to an epigenetic modulator and optionally a differentiation inhibitor. Thus, the techniques provide for HEPARG® reprogramming to stem-like cells (Hepa-SC) in order to set a bank of cells with indefinite cell renewal potentialities.

Methods of directing (re)differentiation of Hepa-SC cells into a target population of reprogrammed cells are also described. The methods generally comprise culturing Hepa-SC cells under conditions of mechanical stress and in the presence of at least one differentiation factor for the desired/target cell population for a time period sufficient for the Hepa-SC cells to commit to differentiation. The committed cells are then transferred to a culture medium comprising the differentiation factor and maintaining the cells in culture without the mechanical stress to yield the reprogrammed cells. Thus, the techniques include methods for Hepa-SC reconversion to hepatic differentiation lineage, such that a potentially unlimited number of reconverted new Hepa-RP cell lines could be obtained. The invention relates to obtaining new Hepa-RP lines originating from the parental HEPARG® cell line, in using a strategy of cell reprogramming to Hepa-SC so that Hepa-RP lines are the first hepatic lines derived from stem-like cells originating from a hepatoma cell line and able to produce mature human hepatocytes. The invention also relates to the capacity of Hepa-RP cells to share similar features with HEPARG® or alternatively to express new biological properties making their functional behavior deeply changed, by modifying culture conditions.

Thus, a new hepatic cell line having the identifying characteristics of Hepa-RP is also described herein. Likewise, the invention is also concerned with a new culture medium for proliferating Hepa-RP cells comprising a basal nutrient medium, L-glutamine, insulin, and optionally at least one cortico-steroid, and DMSO.

BRIEF DESCRIPTION OF THE DRAWINGS

Figure (FIG. 1 shows Hepa-SC cells maintained (A) in the absence; or (B) presence of 10 μm Rho-kinase inhibitor Y-27632 at passage 4.

DETAILED DESCRIPTION OF PREFERRED EMBODIMENTS

Figure 1:
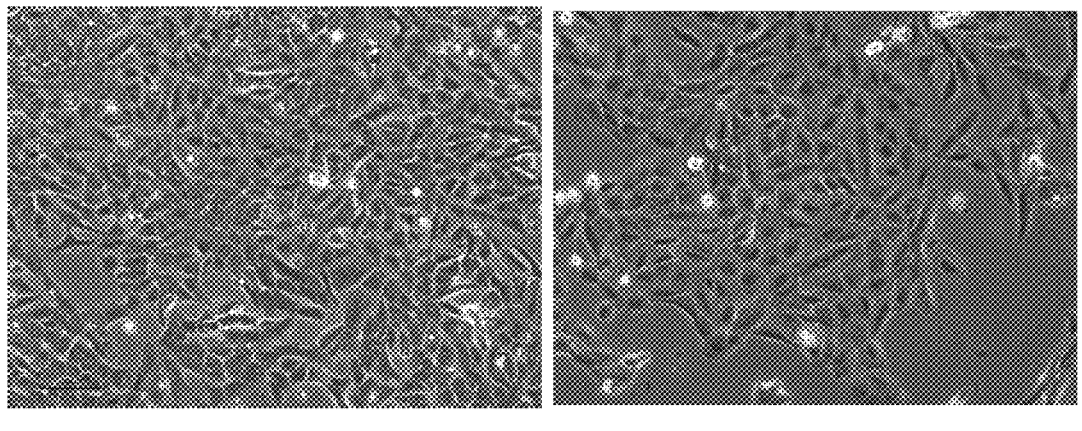

The present invention is concerned with new cell lines. A "cell line" is a population of cells of common origin cultured together after several passages in vitro, such that the cells share generally similar growth rates, morphology, nutritional requirements, and expression markers. The new cells lines are derived from the parental immortalized HEPARG® cell line through transition to stem cell-like cells, designated herein as Hepa-SC cells. The term "derived," as used herein, refers to obtaining new cell types that are distinct from the parental line, through a defined selection and manipulation of the parental cell line, as described below. The invention is concerned with production of new hepatic cell lines, designated herein as Hepa-RP cells. The Hepa-RP cells are derived from the reprogrammed stem-like cells, Hepa-SC, then redirected to hepatic lineage, their phenotype being similar or distinct from the parental HEPARG® cells according to culture conditions. The invention is concerned with new properties expressed by Hepa-RP cells. This invention relates to their uses in biology, pharmacology, toxicology, and prophylactic applications.

The new Hepa-SC cells are defined as stem-like cells derived from the HEPARG® cell line. The Hepa-SC cells are "stem-like," which means that they have characteristics of stemness. Stemness is an essential characteristic of a stem cell that distinguishes it from ordinary cells, and more specifically refers to undifferentiated (unspecialized) cells that have the potential to differentiate into specialized cells, and which are capable of renewing themselves through cell division. As such, cells exhibiting stemness are pluripotent or multipotent self-renewing cells. The term "undifferentiated" as used herein refers cells which have not developed a characteristic of a more specialized cell (e.g., a specific purpose, function, etc.). In contrast, a "differentiated" cell has taken on characteristic of a more specialized cell type. Differentiated and undifferentiated cells are distinguished from each other by several well-established criteria, including morphological characteristics, expression characteristics and/or functional characteristics associated with the specialized function or purpose of a given cell.

One advantage of the invention is that setting Hepa-SC lines capable of expressing stemness properties, mainly self-renewal, represents a virtually infinite source of HEPARG®-like cells carrying the capacity to differentiate into mature human hepatocytes. The stem-like cells of hepatic origin, designated herein as Hepa-SC cells, are characterized by one or more of the following features (which are demonstrated in the working examples and figures). First, the Hepa-SC cells are derived from HEPARG® cells through mechano-transduction techniques described in more detail below. The Hepa-SC cells have a characteristic morphology when seeded at low density, with round and flat shape, with a huge regular nucleus, and a smooth wavy plasma membrane at the borderside. The Hepa-SC cells have a capacity to undergo an epithelio-mesenchymal transition (EMT) during proliferation; the proliferating cell population is composed of elongated (mesenchymal) and polygonal (epithelioid) cells. This property reflects a great plasticity of the cells.

Hepa-SC cells have an active proliferation with a population doubling time period of 20-24 h. Hepa-SC cells also express several stem cell markers such as OCT4, NANOG, low levels of nuclear β-catenin, and the like. Likewise, expression of all differentiation markers associated with HEPARG® are completely extinguished or silent in Hepa-SC cells. Hepa-SC cells also transiently express several growth factor receptors generally associated with early development and morphogenesis (such as TGFβ-R; FGF-R1 and FGF-R2, IGF-R, MET). These extended changes in genes expression are associated with a drastic change from a general hyper-methylated DNA profile characterizing the parental HEPARG® cells to a hypo-methylated one in the Hepa-SC cells. Hepa-SC cells also exhibit a plasticity in response to the physical environment. For example, Hepa-SC cells form flat and spread colonies when cultured on stiff supports such as polycarbonate polymer or polycarbonate layered with collagen, matrigel, or the like. However, Hepa-SC cells are capable of forming spheroids when seeded on thick soft hydrogel such as thick matrigel. Hepa-SC cells are also characterized by a remarkable capacity to redirect a hepatic differentiation lineage after numerous passages (at least about 45 passages) in conditions allowing stem cell properties. For instance, under predefined culture conditions, they give rise to new permanent lines (Hepa-RPs) with recovered bipotent properties such as progression to both hepatocyte and biliary cell lineages, thus mimicking the parental HEPARG® cell line in that respect.

Hepa-SC cells have the capacity to react to mechanical forces such as shape constraint, when plated at very high density. Shape-constrained Hepa-SC cells are preferentially directed to hepatocyte differentiation in presence of insulin and at least one cortico-steroid such as hydrocortisone hemisuccinate, as discussed in more detail below. However, Hepa-SC cells are pluripotent and can also be directed to adult cell types distinct from the hepatic lineage, but common to anterior endoderm such as beta-pancreatic cells and also to be directed to cell types belonging to mesoderm such as osteoblasts. The Hepa-SC cells also have a stable karyotype which advantageously results from the mechano-transduction strategy used for HEPARG® reprogramming to Hepa-SC.

It is interesting to note that the Hepa-SC cell properties contrast with those of progenitors from the HEPARG® parental lines for which long term and active proliferation leads them to lose their capability of undergoing hepatocyte differentiation and of keeping stability of their genome expression (e.g., occurrence of some oncogenes induction). Hepa-SC is a continually proliferating cell line of hepatic origin. This makes Hepa-SC unique as cell type regarding origin and properties.

Described herein are methods of producing stem-like cells of hepatic origin, and specifically for producing Hepa-SC cells. The methods combine mechano-transduction signaling and epigenetic factors, so that the resulting Hepa-SC cells can be defined as reprogrammed stem-like cells created by induction of "stemness" properties through modification of physical environments, mechanical forces, and epigenetics, without introducing additional genes into the genome.

The methods generally comprise culturing the parental cells (HEPARG®) in the absence of differentiation factors. As used here, a "differentiation factor" is an agent known to promote or induce differentiation signaling in the parental cell line. In one or more embodiments, the parental cells are cultured by exposing to a culture medium that is free of differentiation factors for the parental cells. The basal media for the culture media can include any suitable nutrient formulation, such as William's E, or Dulbecco's Modified Eagle's Medium (DMEM)/HamF12, M199/DMEM, Roswell Park Memorial Institute (RPMI), and the like, which culture medium may be supplemented with insulin, L-glutamine, fetal calf serum (FCS), combinations thereof, or equivalent media, and the like. In one or more embodiments, the parental cells are passaged at least two times in the differentiation-factor-free culture medium. More specifically, the parental cells are cultured in a first culture medium that is free of parental differentiation factors for a first period of time (e.g., 1 week or more), and then transferred to at least a second culture medium that is free of parental differentiation factors. In general, the first and second culture media will have the same formulation. Differentiation factors will vary depending upon the target differentiation lineage desired. In one or more embodiments, differentiation factors include cortico-steroids, DMSO, retinoic acid, o-estrogens, thyroid hormones, and/or synthetic analogues thereof. The term "synthetic analogues" is used to refer to the functional analogues of non-natural origin. Exemplary cortico-steroids include hydrocortisone hemisuccinate and/or dexamethasone. As used here, the term "free of differentiation factors" means that such differentiation factors are not intentionally added or included as part of the culture medium, although it will be appreciated that some incidental impurities may exist (such as residual agents that may be present after washing the parental cells before seeding in the first culture medium free of differentiation factors). Thus, the amount of any residual differentiation factor that may be present in the culture media should be less than about $10^{-6}$M and preferably less than about $10^{-7}$M, for example in the case of cortico-steroid, and less than about 0.01% in the case of DMSO.

The cells are then transferred from the at least second culture medium, and subjected to mechanical stress under environmental conditions such that the parental cells revert to stem-like cells. For example, the cells are subjected to physical stress by plating the cells at high density to physically constrain the cells. The cells are subjected to mechanical stress for a time period sufficient to revert the cells to stem-like cells. In one or more embodiments, the cells are plated at a density of from about $1.7 \times 10^5$ cells/cm$^2$ to about $2.2 \times 10^5$ cells/cm$^2$ for about 10 to about 20 hours. As discussed above, the resulting "stemness" of the cells can be verified using various approaches. The mechanical stress generates a reprogramming signal towards stemness associated with a mechano-transduction signaling in the cells in a somewhat synchronized manner, resulting in expression of a detectable "stem cell signature" at the genomic level.

The stem-like cells are then subjected to epigenetic modification to stabilize the stemness characteristics of the cells. Epigenetic modification refers to mitotically heritable changes in gene expression that are not coded in the DNA sequence itself. In general, epigenetic modification involves subjecting the cells to methylation/acetylation modulators; it being appreciated that the selected modulators should neither alter cell proliferation nor provoke toxicity effects or apoptotic induction in the cells. In one or more embodiments, the cells are subjected to a methylation inhibitor in an amount and for a time period sufficient to stabilize the stemness characteristics. In one or more embodiments, the cells are transferred to a container and cultured with culture medium in the presence of the selected modulator. Exemplary modulators include epigenetic factors belonging to the histone demethylase molecules, such as 5-azacytidine and the histone lysine methyltransferase EHMT2, a methylation inhibitor (BIX 01294). Other epigenetic factors belonging to the HDAC family could be also used. 5-azacytidine is a preferred modulator, when used at a dose which does not inhibit cell proliferation and does not induce visible cell toxicity. 5-azacytidine could be used in the stabilization medium at concentrations of about from about 1 to about 10 μM, preferably from about 5 to about 10 μM, and more preferably about 10 μM. BIX 01294 can alternatively be used, but may induce higher cell toxicity.

The stabilized cells are then allowed to grow and proliferate. Conditions for growth and proliferation are favored by culturing the cells in the presence of exterior signaling that blocks the engagement of differentiation. In one or more embodiments, the cells are cultured in the presence of a differentiation inhibitor. In one or more embodiments, differentiation inhibitor is added to the stabilization culture medium. Suitable differentiation inhibitors include protein kinase inhibitors, such as RHO-kinase inhibitors (e.g., Y-27632, fasudil, effectin, etc.), GsK3 inhibitors (e.g., CHIR 99021), and the like. When Y27632 is used, the concentrations of about 5 and about 10 μM can be used in the culture.

Advantageously, the selected culture conditions allow long term production of the stem-like cells without loss of their stemness fate. Many passages (at least 50 passages) have been successfully stably produced. Thus, in one embodiment, the method comprises continuously exposing the stem-like cells to a medium comprising at least one methylation/acetylation modulator and being free of a corticosteroid. In one embodiment, the invention also provides a maintenance medium suitable for maintaining the stability of the Hepa-SC cells. The Hepa-SC maintenance medium comprises a basic cell nutrient media, supplemented with L-glutamine, insulin (10 µM), and 5-aza-cytidine, and is free of a differentiation factor (e.g., cortico-steroid). Exemplary basic cell nutrient media includes William's E, RPMI, DMEM/HamF12 (3/1), or DMEM/MEM199 (3/1), and the like. This basic nutrient medium is added with L-Glutamine or preferentially, Glutamax, and contains insulin (from about 5 to about 10 µM, preferentially about 10 µM) and 5-aza-2'-deoxycytidine (from about 2.5 to about 10 µM, preferentially about 10 µM). The nutrient medium can also contain about 10% FCS. Optionally bFGF (about 40 ng/ml) and EGF (about 20 ng/ml) plus essential fatty acids can be used when decreased FCS concentration (about 0.5 to 2% instead of 10%) is desired.

Advantageously, the Hepa-SC cells are capable of differentiating into other cells. In one embodiment, methods of directing cell differentiation of Hepa-SC cells are described. The methods generally comprise culturing the Hepa-SC cells in the presence of a differentiation factor and under mechanical stress to commit the cells towards the target cell population. More specifically, Hepa-SC cells in culture are first washed to remove the methylation/acetylation modulators and maintenance culture. The washed Hepa-SC cells are then subjected to mechanical stress, such as by plating at a high density. The culture medium used for plating is preferably a proliferative medium for the target differentiated cell type. In the case of commitment towards differentiation into hepatic cells, the proliferative medium preferably comprises basic cell nutrient medium, supplemented with insulin, and at least one differentiation factor for hepatic cells. In one or more embodiments, the differentiation factor is a cortico-steroid at a non-toxic concentration which promotes differentiation. The phrase "non-toxic concentration which promotes differentiation" is used to refer to the cortico-steroid concentration promoting, during its addition to a culture of Hepa-SC, the differentiation of the cells towards a hepatic morphology and a functional state. This concentration is non-toxic, i.e. its addition does not lead to a cell mortality rate greater than approximately 10%. The cells are cultured under mechanical stress for a sufficient period of time to reach confluence and for commitment of the cells to differentiation, as recognizable by morphological features. The cells are then transferred from the high density plating container and further cultured at low density in the same proliferative medium. The resulting cells are designated herein as Hepa-RP cells.

According to the present invention, the Hepa-RP cells when cultured in conditions defined for HEPARG® (as described in U.S. Pat. No. 7,456,018), have a functional behavior resembling HEPARG®, thus making sustainable production of HEPARG®-like cells for long term use. These new cell lines, designated herein as Hepa-RP, are characterized by a typical morphology described for hepatic progenitors at low density, with a mixed population of elongated and polygonal cells as found in the originating HEPARG® line. However, they are also characterized by the presence of numerous cells with round and flat shape, with a large regular nucleus, and a floating plasma membrane at the periphery corresponding to the description of the parental Hepa-SCs. The Hepa-RP cells also have an active proliferation with a population doubling of 24 h, but a delayed contact inhibition response compared to HEPARG® cells. The Hepa-RP cells are also characterized by bipotent properties so that cells can be further directed to hepatocyte or primitive biliary cell lineages and 2 distinct cell types, hepatocytes and primitive biliary cells. Likewise, the Hepa-RP cells have the capacity to undergo a complete differentiation program to mature hepatocytes as the originating HEPARG® line. In one or more embodiments, the Hepa-RP cells are maintained in medium comprising at least one cortico-steroid. The medium is further supplemented with DMSO in a quantity sufficient to induce differentiation. The term "quantity sufficient to induce the differentiation" is used to refer to the quantity of DMSO necessary to induce the differentiation of a culture of normal human hepatocytes. In one or more embodiments, the cells are cultured in the presence of a cortico-steroid, followed by exchanging the medium for one further supplemented with DMSO as described above. The cells are cultured for a sufficient time period such that the differentiation factor(s) directs maturation of the cells into the target population of hepatocytes. The differentiation factor is present at a non-toxic concentration which promotes the differentiation of hepatocytes (e.g. DMSO at from about 1% to about 2%, and preferentially about 1.5%). The resulting differentiated cells can then be maintained in this same medium.

Typical polarized morphology is observed in the Hepa-RP cells with formation of bile saccular and canalicular structures characterized by specific transporters localization. The Hepa-RP cells also have the ability to express the different hepatocyte markers as in HEPARG® with minor variations in the expression levels such as APOA1. Thus, it will be appreciated that the Hepa-RP cells have preserved the same karyotype as HEPARG®.

However, transition through Hepa-SC status has introduced a few changes in the methylation/acetylation profile of some genes in the Hepa-RP cells. Thus, the new Hepa-RP cell line is distinct from HEPARG® cells in several characteristics. For example, the Hepa-RP cells do not exhibit multilayering, even after 2-3 weeks of differentiation, a characteristic which evidences new cell interaction properties. This feature will provide to Hepa-RP great advantages for all imaging analysis applications. The Hepa-RP cells also have a capacity to organize a gradient of differentiating hepatocytes around numerous circular empty zones randomly formed within the monolayer culture. This organization could advantageously mimic the gradient which is characteristic in the liver lobule in vivo and defining a periportal and a centrolobular zones. Importantly, this property has never been observed with HEPARG® cells.

Hepa-RP cells also have a reduced sensitivity to DMSO for conditioning the completion of hepatocyte differentiation. This means that cells have acquired the molecular regulations indispensable for progressing through this program without introducing environmental influence such as exposure to toxic agent as DMSO. This property could provide great advantage to the cell line particularly in toxicological and pharmacological applications.

The Hepa-RP cells have increased stability through passages which can be improved regarding their capacity to form hepatocyte colonies. This has been further improved through the addition of low concentration of DMSO into the medium early during the proliferation stage. At these low concentrations of DMSO, the cells preserve a high growth activity while occurrence of heterogeneous cell colonies is inhibited.

Accordingly, in one embodiment, the invention also covers the use of the new proliferating medium for Hepa-RP proliferation comprising a basal medium as defined above added with L-glutamine (preferably Glutamax), insulin, and at least one cortico-steroid, and containing low concentration (not exceeding 0.2%) of DMSO during the first stage of proliferation corresponding to the 3 first days post-seeding, followed by the same medium containing moderate concentrations (not exceeding 0.5%, preferentially 0.4%) of DMSO up to the use of the differentiation medium. This combination allows maintenance of Hepa-RP cells in conditions for obtaining behavior similar to that of HEPARG®.

Again, as noted above, the Hepa-RP cells are likewise distinct from HEPARG® cells, and have a high plasticity. The Hepa-RP cells are sensitive to environmental conditions in their ability to control differentiation programs. Unexpectedly, when maintained under different culture conditions (from those established for HEPARG® cells), the Hepa-RP cell line can be cultured to achieve different fundamental features.

Advantageously, the Hepa-RP cells can be cultured and stably expanded in culture medium that is free of differentiating factors e.g., free of any cortico-steroid and of DMSO. In the corticoid-free medium, the cells can be cultured for several passages (more than 15 passages, preferably more than 18 passages), but evidence the stable ability to rapidly respond to corticoid signaling (preferentially hydrocortisone hemisuccinate) when added to the culture medium, in order to direct hepatocyte differentiation program. DMSO (from about 1% up to about 1.5%) is then added for completing hepatocyte maturation. This corticoid-free culture condition for Hepa-RP cell expanding is new.

These new culture conditions advantageously allow improving the stability of the cells which can be maintained more than 35 passages in very simple culture conditions, and keeping their capacity to respond to corticoid signaling and to undergo a complete differentiation program even in presence of low DMSO concentration. Such stability was never reached before so that these culture conditions could represent a strategy for supporting or improving the cell lines stability. The foregoing approach can be used to prolong the stability of Hepa-RP cultured in standard conditions beyond 18 passages and up to 35 passages. In the work carried out, the functional potentialities of the hepatocytes appeared high and completely normal.

These new corticoid-free expanding conditions drastically and spontaneously lead to increasing the proportion of hepatocytes in the cultures exposed to corticoids, up to reach purity of the population in hepatocytes. However, the new corticoid-free expanding conditions lead to a gradual reduction (in 2-3 passages) of the bipotent property when the Hepa-RP cells do receive the corticoid signal, which was a main characteristic of HEPARG®. It is surprising to observe a disappearance of clear primitive biliary cells (e.g., the resulting culture is essentially free of biliary cells). This event is also accompanied by a strongly delayed and partial loss of reversion of Hepa-RP hepatocytes to progenitor cells in contrast to HEPARG® cells, which makes the cell model much more reproducible and easier to use for end-users. In one embodiment, these corticoid-free expanding conditions represent conditioning for producing Hepa-RP in an undifferentiated status, distinct from the progenitor cell status characteristic for HEPARG®, giving real advantages in successfully directing Hepa-RP cells to cholangiocyte differentiation program or other programs such as pancreatic or intestinal "routes," distinct from the hepatocyte one. Altogether, these new functional behaviors and new properties of Hepa-RP lines make them distinguishable and original from HEPARG®.

In one or more embodiments, the pluripotent Hepa-SC cells can be directed towards differentiation of non-hepatic cell populations. Exemplary non-hepatic target cell populations include beta-pancreatic cells, enterocytes, osteoblasts, and the like. It will be noted that hepatic and pancreatic cells both originate from the anterior endoderm, whereas enterocytes originate from the posterior endoderm, and osteoblasts as hemopoietic cells originate from the mesoderm lineage. The methods generally comprise culturing the Hepa-SC cells in the presence of a differentiation factor and under mechanical stress to commit the cells towards the target cell population. More specifically, Hepa-SC cells in culture are first washed to remove the methylation/acetylation modulators and maintenance culture. The washed Hepa-SC cells are then subjected to mechanical stress, such as by plating at a high density. The culture medium used for plating is preferably a proliferative medium for the target differentiated cell type. In the case of commitment towards differentiation into beta-pancreatic cells, designated herein as beta-RP cells, the proliferative medium preferably comprises DMEM-low glucose, Activin 10 µg/ml, Epidermal growth factor 20 ng/ml (EGF), Fibroblast growth factor 10 ng/ml (FGF), nicotinamide 10 mM, B27 complement 2%, and L-glutamine 2 mM. It is a serum-free medium. After 20 hours, Hepa-SC cells can be detached and re-seeded at a density of about $4\times10^5$ cells/cm$^2$ on low attachment plates or on plates coated with soft matrigel, and in the same proliferative medium containing at least one factor for directing beta-pancreatic differentiation lineage. In one or more embodiments, the differentiation factor is retinoic acid at a non-toxic concentration which promotes differentiation. The concentration of retinoic acid is from about 2 µM to about 10 µM and preferentially about 10 µM, with an exposure time of from about 15 to about 30 hours, and preferentially about 24 hours. The committed cells are then expanded and allowed to proliferate in medium that is free of the differentiation factor. The cells can be cultured under conditions allowing them to form three-dimensional spheroids (e.g., thick matrix support, such as matrigel or collagen), or they can be plated as a monolayer on a stiff support.

In the case of commitment towards differentiation into enterocytes, the proliferative medium preferably comprises a basic cell nutrient medium which includes William's E or RPMI or DMEM/HamF12 (3/1), and at least one differentiation factor for enterocytes. The proliferative medium preferably comprises HamF12/DMEM-low glucose, Activin 10 µg/ml, Fibroblast growth factor (FGF) 10 ng/ml, B-27 complement 2%, L-glutamine 2 mM, and 2% FCS. After 20 hours, Hepa-SC cells can be detached and re-seeded in the proliferative medium at a density of about $4\times10^5$ cells/cm$^2$. The medium also contains at least one factor for directing enterocyte differentiation lineage. Exemplary differentiation factors for enterocytes include a complex of small factors: mainly the R-spondin which specifically binds to the Leucine-rich repeat-containing G protein-coupled receptors 4-6 (LGR4-LGR6). R-spondin is also one of the potent Wnt agonists that exert profound trophic effects on Wnt-driven stem cells compartments. In one or more embodiments, R-spondin and/or GSK-3 inhibitor XV such as CHIR 99021, Rho-kinase inhibitor, Y-27632 which improves cell recovery and MEK/ERK inhibitor such as PD98059 are main factors contributing to direct the differentiation lineage to enterocyte. The same protocol as for beta-pancreatic cells can be followed. In more detail, after the shape constraint signal Hepa-SC cells can be split and suspended in a medium containing the cocktail of factors described above and then, distributed to wells.

In the case of commitment towards differentiation into osteoblasts, the proliferative medium preferably comprises DMEM high glucose, 10% FCS, dexamethasone 10-7M, and 25 µg/ml ascorbic acid. At confluence, after around 14 days they develop an extracellular reticular network on which calcium concretion (one of differentiation markers) are formed (positive to ALIZARIN test).

The new cell lines, both Hepa-SC and Hepa-RP, have a variety of uses. For example, the new cell lines can be used for the production of long term stably-recombined cell lines from re-differentiating cell lines such as Hepa-RP.

The new cell lines, or differentiated cells derived therefrom can be used in the production of three dimensional spheroids using an easier and more scalable technique that relies on physiological influences, as compared to existing three-dimensional molding techniques (e.g., hanging drop method, etc.). For example, the techniques described herein use morphogens that make the cells "contract" the cytoskeleton to form three dimensional spheroids.

The new Hepa-RP cell lines can be used for preparing bioreactors using a more scalable technique and taking advantage of higher stability of these cells.

The cells can also be used in drug screening assays, assays related to infectious diseases (e.g., HBV, HCV, *plasmodium*), studies on apoptosis and aging, and the like. The cells are also advantageous for procedures involving imaging analysis, since the cells form a regular monolayer. The Hepa-SC cells can be used for assays as representative of the resident stem cells in the liver, and tested as targets for drugs or toxic agents, leading to alterations responsible for tumorigenesis. Likewise, Hepa-SC cells can be used to study anticancer drugs and evaluate therapeutic agents that can direct cancer stem cells to a differentiated phenotype and away from metastasizing.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Methods for Producing Stem-Like Cells Such as Hepa-SC

The new method for reprogramming and producing stem-like cells involves subjecting cells with transdifferentiation properties in vivo and/or in vitro such as HEPARG® cells to predefined conditions, so that they start to lose their differentiation status.

A. The General Process for Inducing "Stemness":

Step 1: Culturing the parental cells in a culture medium that has been modified in order to eliminate all factors supporting differentiation processes during a 2-passage culture period;

Step 2: Inducing mechanical stress such as shape constraint, onto the cells in order to generate a reprogramming signal toward stemness that should be associated with occurrence of a mechano-transduction signaling in all the cells in a synchronized manner, resulting in expression of a "stem cell signature" at the genome level;

Step 3: Inducing the stability of this stem cell fate by epigenetic mechanism, for instance by exposing the cells to methylation/acetylation modulators such as HDAC molecules. Epigenetic modifications refer to mitotically heritable changes in gene expression that are not coded in the DNA sequence itself (Levenson J M, Sweatt J D., 2005). The chosen epigenetic molecule should neither alter cell proliferation activity nor provoke toxicity effects and/or apoptotic induction. 5-azacytidine inhibits DNA methylation. It has been preferentially chosen for HEPARG® reprogramming to Hepa-SC stem-like cells after comparative study with Bix 01294, a small molecule known to inhibit the histone H3 methylation. It is sometimes considered to replace oct 3/4 (Chang Y et al., 2009)—one of the four original genetic factors used for reprogramming of mammalian somatic cells into induced pluripotent stem (iPS) cells. Bix 01294 appeared much more toxic even at low concentration in our culture conditions.

Step 4: Favoring the cell survival and growth of stem-like cells while blocking engagement to any differentiation lineage in exposing the cells to exterior signaling, mainly related to protein kinase pathways. Two main factors have been tested: 1) Rho-kinase inhibitor which inhibits all differentiation processes, favors cell survival, growth and spreading. Different concentrations of ROCH (Y27632) have been tested, from 0.5 to 20 µM. The concentration of 10 µM has been preferentially chosen and added to the culture medium during Hepa-SC cell line establishment and maintained for the 5-6 first passages. Other forms of inhibitors could be used such as fasudil or effectin. 2) Another factor, CHIR 99021, known as a specific substrate of GsK3, is a protein kinase inhibitor that can be chosen for its capacity to inhibit the GsK3 pathway involved in differentiation through its relationship with the Wnt/β-catenin pathway (Ying Qi-L. et al., 2008).

B. According to the Following Defined Method, HEPARG® Cells are Advantageously Reprogrammed to Stem-Like Cells (Hepa-SC) without Introducing Additional Genes to their Genome.

Step 1: HEPARG® progenitors are maintained in a medium deprived of hydrocortisone for one week or more and replated once in this medium;

Step 2: Reprogramming is performed by plating the cells at very high density in order to induce a shape constraint (for instance 800×103 cells per well of 24 well-plates) for 10 to 20 hours. A period of time of 20 hours has been preferentially chosen.

Step 3: Cells from each well, are detached and divided into 2 or 3 wells. Stabilization of the genome of the reprogrammed cells is obtained by adding 10 µM 5-azacytidine. 5-azacytidine could be used at concentrations of about 1, about 5 or about 10 µM. However, the highest concentration of 10 µM has appeared more relevant regarding the stability of the new lines throughout 40 passages.

Step 4: Increased stability and increased proliferation is favored by the addition of 10 µM RHO-kinase inhibitor.

C. Culture Conditions Favoring the Stability of the Hepa-SC Cells During Long Term Culturing (at Least 50 Passages).

Absence of cortico-steroid and permanent exposure to an epigenetic factor capable of stabilizing the genome expression by controlling the methylation/acetylation levels of the genes, have been proposed. 5-aza-2'-deoxycytidine has been preferentially used at 10 µM, a dose which does not inhibit cell proliferation and does not induce visible cell toxicity (Seeliger C. et al., 2013). —Moreover, cooperation between the epigenetic treatment and the RHO-kinase pathway inhibition (Y-27632) has been chosen for increasing the number of stem-like cells in the population, for improving their survival and for inhibiting their entry in any differentiation program (Watanabe K, Ueno M et al., 2007).

Cells are maintained in the William's E medium added with insulin, 5-azacytidine (10 µM) and Y-27632 (10 µM) and 10% Fetal calf serum) for the 10 first passages. Every 10 days, when cells are reaching subconfluence, the cultures are passaged by diluting the cells up to 5-6 fold. FIG. 1 shows the results of maintaining Hepa-SC cells in the absence (a) or presence (b) of 10 µM Y-27632 at passage 4. Under these conditions, Hepa-SCs actively grow. Master and working banks have been settled. Four batches have been produced up to now (Hepa-SC1 to Hepa-SC4). Stability of one of them, Hepa-SC1, has been verified up to passage 50 till now. Karyotyping of Hepa-SC1 has been performed up to passage 40 using chromosomic classification and total CGH array analyses; no major change could be detected except a slight increased percentage of mitotic figures with chromosome 8 monosomy.

Example 2

Figure 2:
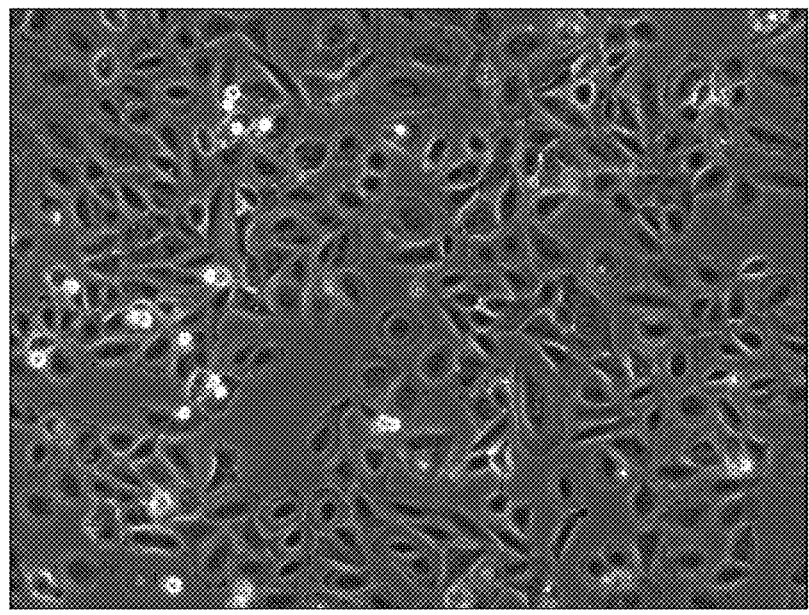
FIG. 2 is a phase contrast micrograph image of a representative population of Hepa-SC cells at low density, 2 days after replating, at passage 2.

Characterization of Hepa-SC Cells Originating from HEPARG® and Maintenance of the Line in Long Term Culture Hepa-SCs Characteristics:

FIG. 2 shows a phase contrast micrograph of a typical population of Hepa-SCs at low density, 2 days after replating, at passage 2. The cells were maintained in the culture medium (William's E+insulin, —Hydrocortisone, +10 µM 5-azacytidine) added with 10 µM ROCK (Rho-kinase inhibitor Y-27632). As can be seen from FIG. 2, the cells exhibit a typical hepatic morphology at low density, with round and flat shape, with a huge regular clear nucleus containing several small nucleoli, and a smooth wavy plasma membrane at the borderside.

Figure 3:
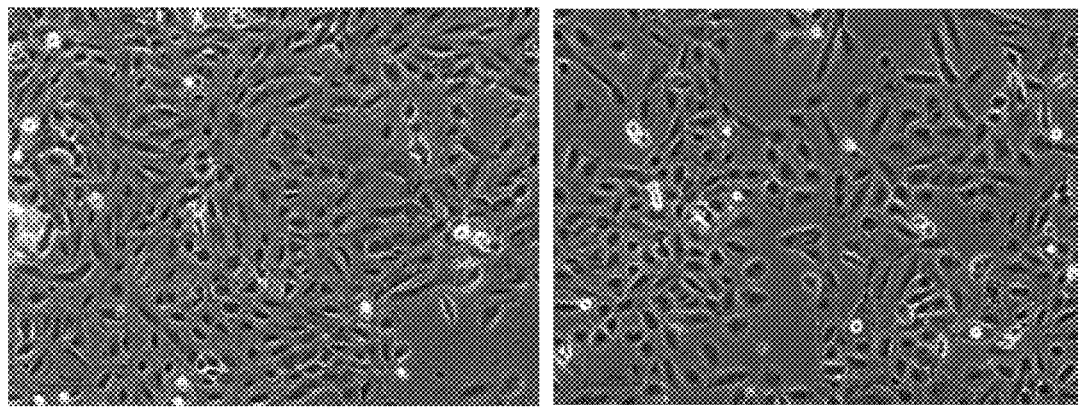
FIG. 3 shows Hepa-SC cells (A) proliferating at passage 3 and (B) proliferating at passage 20, with elongated cells during proliferation visible.

The cells were evaluated for their capacity to undergo epithelio-mesenchymal transition (EMT) during proliferation. FIG. 3 shows phase contrast micrographs of proliferating Hepa-SC cells at passage 3 (A) and 20 (B). Note the high homogeneity of the population and the richness in stem-like cells throughout numerous passages. White arrowheads indicate elongated cells during proliferation. The same medium was used as in FIG. 2. The proliferating cell population is composed of elongated (mesenchymal) and polygonal (epithelioid) cells. This property reflects a great plasticity of the cells which is maintained in long term culture.

Figure 4:
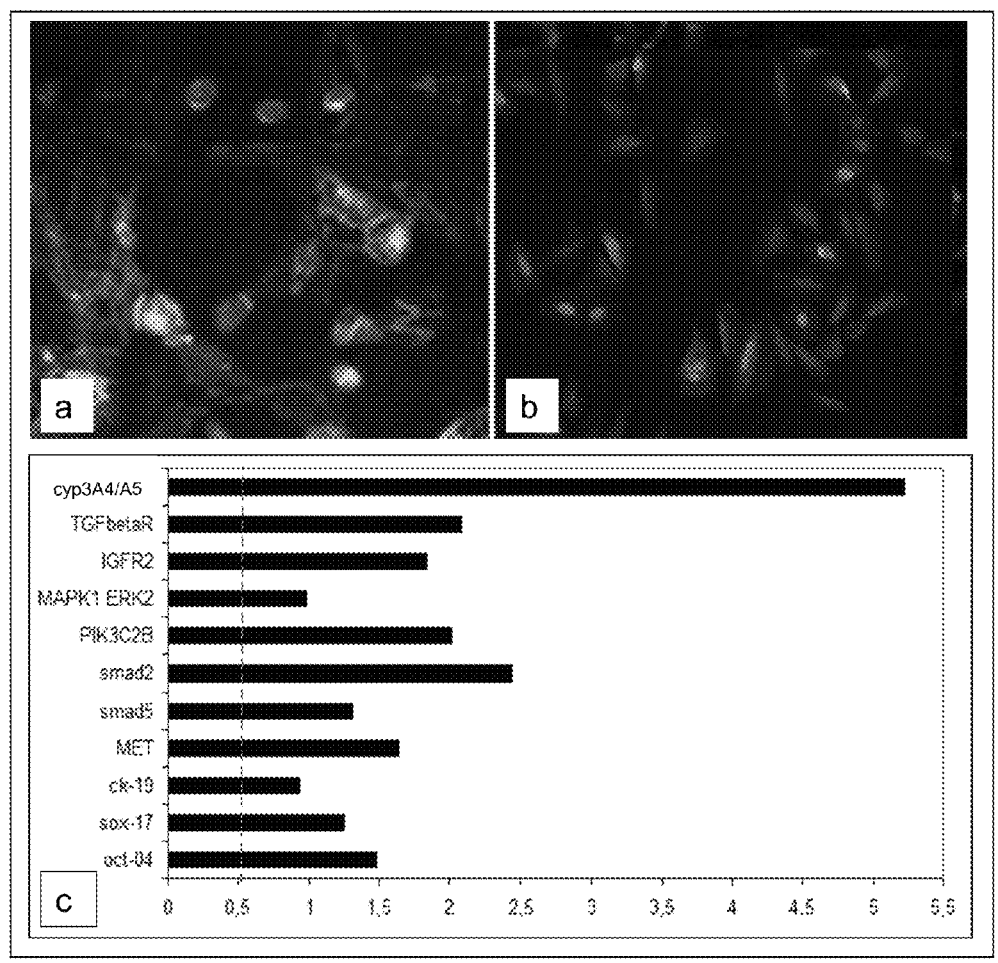
FIG. 4 shows images of the immunolocalization of (A) β-catenin; and (B) oct4 in the nuclei, as well as (C) a graph of the genes involved in morphogenesis by qPCR.

After being subjected to the 20 h shape constraint treatment, the cells were analyzed for expression of different stem markers such as OCT4, NANOG, SOX 17 (early endoderm commitment), etc. and nuclear β-catenin, whilst all differentiation markers are completely extinguished or silent. As seen in FIG. 4, aldolase B, albumin, apolipoprotein A1, CYP3A4, etc. genes are silent as shown at the mRNA level (RT-PCR analysis) while CK19, c-MYC, h-TERT, etc., genes are highly active compared to HEPARG® and Hepa-RP progenitors. FIG. 4 shows immunolocalization of β-catenin (a) and oct4 (b) in nuclei. Panel (c) shows the expression of different genes involved in early development and morphogenesis by quantitative PCR. Results are expressed in fold changes above 0.5 (red basal line) of cells submitted to shape-constraint versus normal progenitors.

Figure 5:
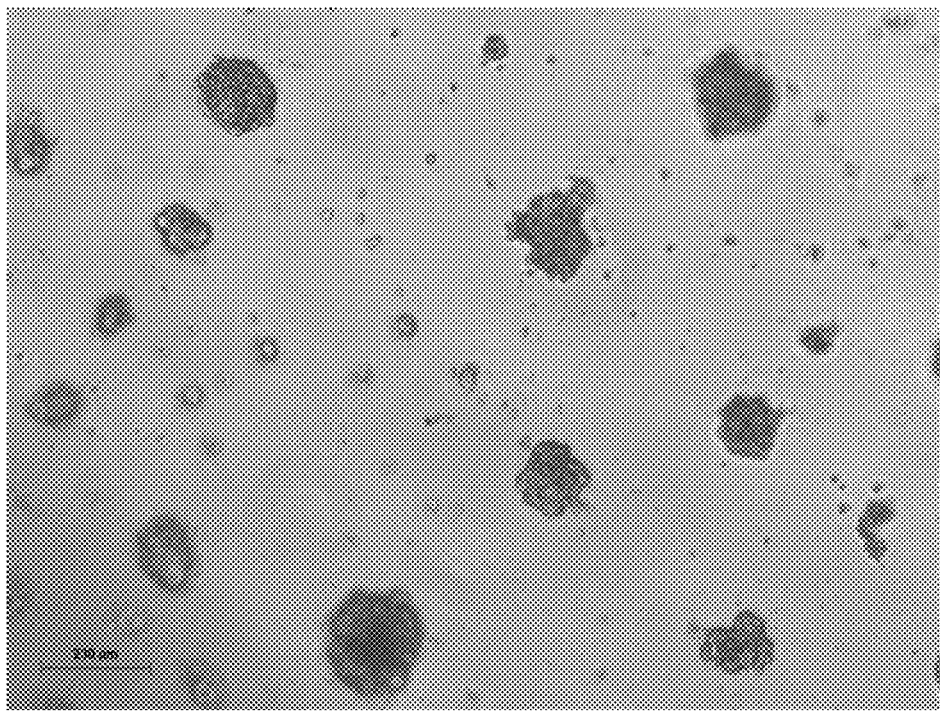
FIG. 5 is a phase contrast micrograph of spheroids formed 6 weeks post seeding on matrigel.

The influence of mechanical factors on the Hepa-SC cells was analyzed. A volume of 100 µl of cold matrigel solution (Beckton Dickinson) prepared at the preferential concentration of 9 µg/ml was deposited per well of a 24 well-plate in a cold room. A soft gel of 300-500 µm was formed at room temperature. 2 to 4 hours later, Hepa-SC cells were seeded preferentially at 800×10$^3$ cells per well in presence of retinoid acid (10 µM). Spheroids formation was observed after 15-20 hours. The spheroids were maintained thereafter in the complete William's culture medium containing insulin and corticoid (hydrocortisone hemisuccinate), without retinoic acid for at least 2 weeks. FIG. 5 shows a phase contrast image of the spheroids 6 weeks post-seeding. Their high plasticity in response to environmental supports is characteristic: Hepa-SCs form flat and spread colonies on stiff supports such as polycarbonate plate or polycarbonate thinly layered with dry collagen I. In contrast, as shown in FIG. 5, Hepa-SCs form spheroids on thick soft hydrogel such as matrigel.

As shown in Example 1, the Hepa-SC cells also have the capacity to react to mechanical forces such as shape constraint, by plating the cells at very high density. Shape-constrained Hepa-SCs are preferentially directed to hepatocyte differentiation in presence of insulin and cortico-steroid.

As demonstrated in Example 3 below, the Hepa-SC cells also have the capacity to redirect a hepatic differentiation lineage after many passages (45 tested) as stem cells and to give rise to new permanent lines with recovered bipotent properties such as hepatocyte and biliary cell lineages.

Likewise, as demonstrated in Example 6, the Hepa-SC cells also have pluripotency properties as shown by their capacity to be directed to adult cell type distinct from the hepatic lineage but common to anterior endoderm such as beta-pancreatic cells and also to be directed to cell type belonging to mesoderm such as osteoblasts.

Example 3

Procedure for Directing Hepa-SC to Distinct Differentiation Programs

A. The General Principle of the Inventive Technique:
  Step 1: Shape-constraint signal: Hepa-SCs are seeded at very high density ($8\times10^5$) in the medium used for their propagation, as described in Example 1, except the epigenetic factor (5-aza) is discarded.
  Step 2: Detachment of the cells by trypsin and reseeding at $4\times10^5$ either onto thick soft matrigel or other hydrogel, or stiff supports.
  Step 3: Influence of the main morphogen factor needed for directing the differentiation pathway, added to the appropriate medium used for cell maintenance often enriched with various other growth factors.

Figure 6:
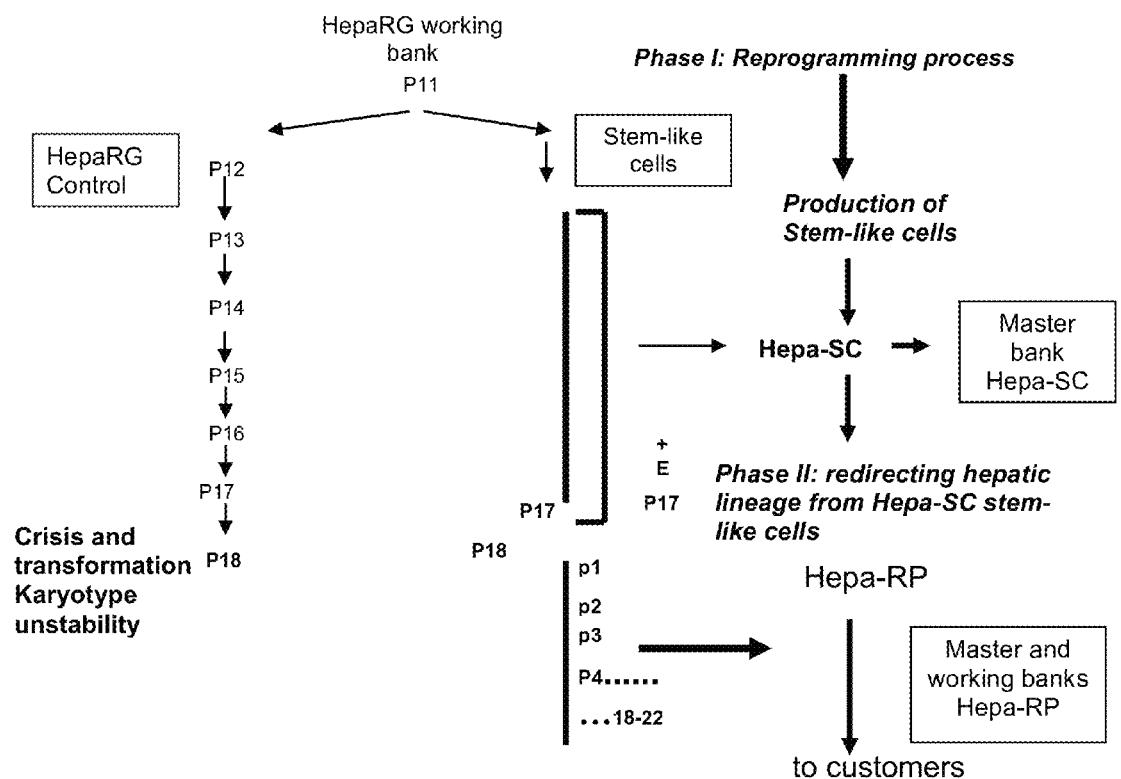
FIG. 6 is a flowchart of the protocol used for production of the Hepa-RP cells from the HEPARG® cells, transitioned through stem-like Hepa-SC cells.

B. Example of Differentiation Programming of Hepa-SC to Hepatic Lineage:

In this Example, a specific reprogrammed Hepa-SC line, designated as Hepa-RP3, is described. FIG. 6 illustrates an overview of the process flow for generating the reprogrammed hepatic line (Hepa-RP). Hepa-SC cells were submitted to a new method designed for redirecting the cells toward the hepatic differentiation route. Subconfluent Hepa-SC cells maintained in William's E medium added with 5 µM 5-azacytidine were washed twice with PBS to eliminate serum and 5-azacytidine. The cells were then detached with 0.05% trypsin. The cells were collected in the proliferative medium used for HEPARG® cell line. Briefly, this medium includes the William's E medium as basic nutrient medium, added with L Glutamine or preferentially, Glutamax, and contains insulin (from 5 to 10 µM, preferentially 1004) plus 50 µM hydrocortisone as cortico-steroid. The cells where seeded at high density (400,000/well in a 24-well plate) in order to induce mechanical stress. After 20 h, the cells were detached and reseeded at a low density on plastic with the same proliferating medium.

The foregoing process allows the Hepa-SC cells to lose their stem-like status and to retrieve the hepatic lineage including both their bipotent property and their capacity to undergo a complete hepatocyte differentiation process.

Figure 7:
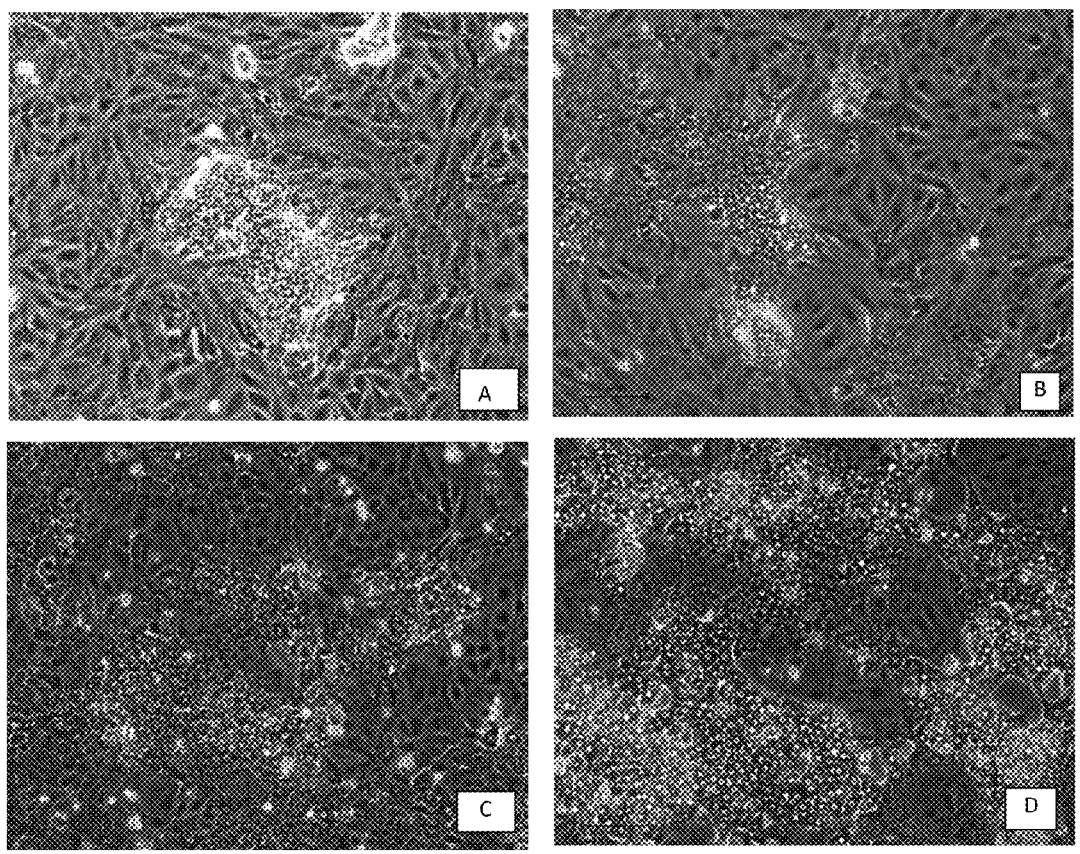
FIG. 7 shows images of the Hepa-RP cells at (A) passage 1; (B) passage 2, plus 0.5% DMSO; (C) passage 6; and (D) passage 9, plus 0.5% DMSO.

The retrieval was performed in one step (one passage and 8 days). FIG. 7 show images of Hepa-RP3 cells at: (A) passage 1, (B) passage 2+0.5% DMSO; (C) Passage 6; and (D) Passage 9+0.5% DMSO. Changes of the cell shape occur in several foci indicating commitment of some cell colonies toward hepatic cell differentiation program. Response to DMSO is also restored. Hepa-RP3 cells have been directed to undergo a complete process of hepatocyte differentiation from the Hepa-SC stem-like cells. This new cell line has recovered the main characteristics of the parental cells including a bipotent progenitor stage corresponding to a proliferative stage, and a differentiation stage leading to the organization of mature hepatocyte colonies. Although common properties are shared with the parental HEPARG® cells, Hepa-RP3 cells have developed their own characteristics. A master and a working bank have been performed by expanding the cells for 3 passages.

B. Cryopreservation

After detachment with 5 min trypsin treatment cells were put in suspension in proliferating medium and numbered. $1\times10^6$ cells were distributed per vial in 1 mL of cold medium added with 10% DMSO. Vials were maintained on ice, rapidly placed in a freezer at −80° C., then, put in liquid nitrogen for 6 h (or more).

C. Protocol for Maintenance of Hepa-RP3

Hepa-RP3 cells were maintained using a basal medium composed of William's E medium added with antibiotics (peni/strepto), insulin, hydrocortisone at 50 µM, and 10% FCS.

The cryopreserved Hepa-RP3 cells were rapidly thawed and dispersed in a 25 cm² flask containing 3 mL of basal medium. Six to 8h later cells were observed to have attached and medium was renewed with the proliferating medium described above. Medium was changed every 2-3 days thereafter.

1. Maintenance of the line in conditions for obtaining cell behavior similar to HEPARG®.

The cells were maintained under conditions developed to achieve cell behavior similar to HEPARG® cells for up to 20 passages. At each passage, cells were seeded at a density of 26,500 cells per cm² in the proliferating medium containing a low concentration of DMSO (0.2%). The cells attached in 2-3 hours and grew actively for reaching confluence in 4-5 days. Two days after seeding and before reaching confluence, the proliferating medium was added with a higher concentration of DMSO, preferentially 0.5%. After 10-12 days, the cells were highly confluent and ready for replating or for undergoing differentiation.

Replating of the cells was performed every 10-12 days. Cells were washed once with PBS and then incubated with trypsin-EDTA (0.05%) at 37° C. for 3-5 min. Detached cells were collected in the proliferating medium and the suspension was processed for cell numbering using trypan blue solution.

2. Hepatocyte differentiation protocol: 10-12 day old confluent cells were changed with the differentiation medium containing 1 or 1.5% DMSO. After 3-4 days, numerous colonies of cells had committed to differentiation and after one week, they were easily recognized by typical hepatocyte morphological features. The differentiation medium included the proliferative medium containing hydrocortisone and added with DMSO at 1 or 1.5% final concentration.

Because of the presence of DMSO in the medium, we have observed that a cell selection could occur for 4-5 days as evidenced by the numerous dead cells floating into the medium. After one week, the cell monolayer is stabilized and composed of 2 highly distinct cell types, granular differentiated hepatocytes surrounded by clear flat epithelial cells (primitive biliary cells). Maturation needs 4-5 more days to reach completion. Medium was renewed every 2-3 days. In such conditions the monolayer remains confluent and stable for 2 weeks or more.

D. Functional Characteristics

1. Morphology of Hepa-RP3 Cells at Different Stages of the Culture

Figure 8A:
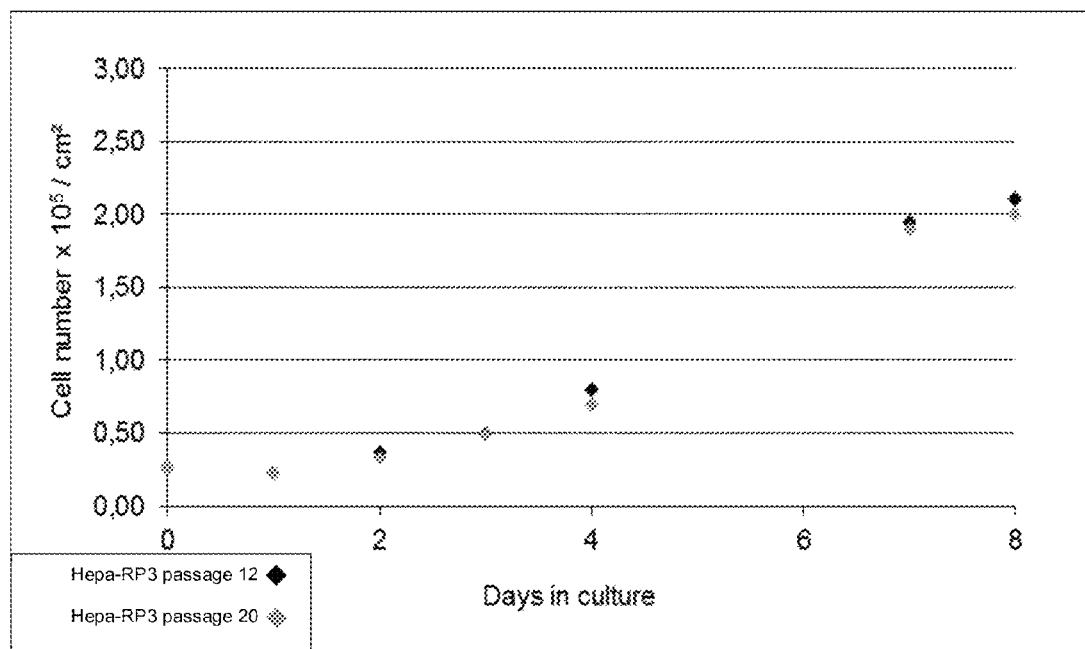
FIG. 8A shows a graph of the growth of the new Hepa-RP3 cells at passage 12 and 20.
Figure 8B:
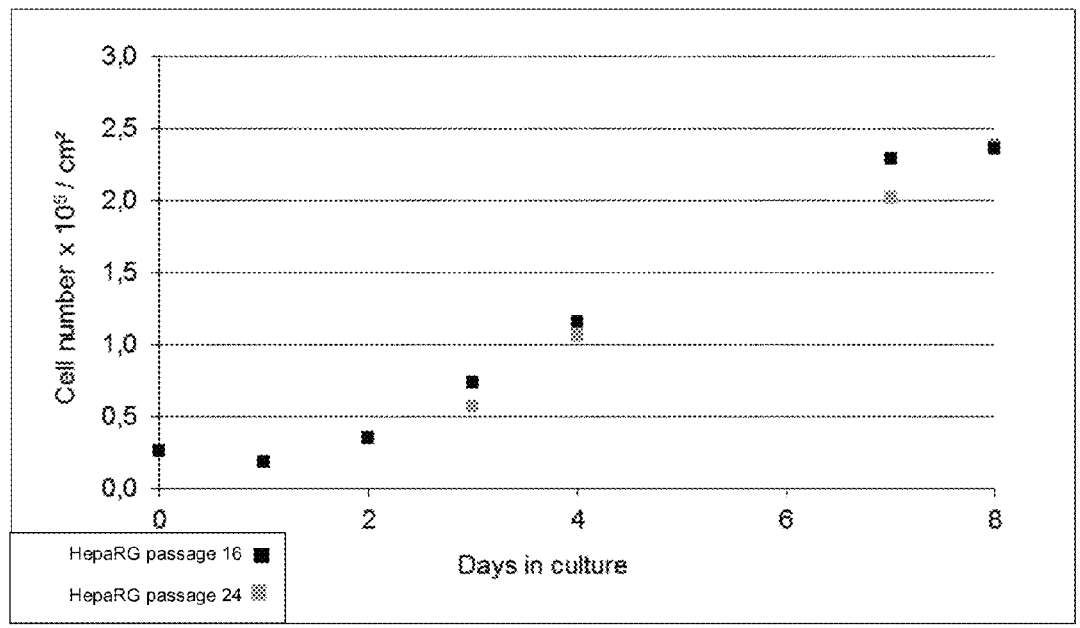
FIG. 8B shows a graph of the growth of HEPARG® cells at passage 16 and 24.

In good culture conditions, colonies of hepatocytes are expected to cover 50% of the surface of the monolayer and sometimes more. Hepatocytes are characterized by a dense cytoplasm when analyzed on phase contrast micrograph, with round nucleus and one dense nucleolus. Numerous typical formations of bile canaliculi were observed. As shown in FIGS. 8A-8B, Hepa-RP3 cells appear to grow faster than conventional HEPARG® cells. An active proliferation with a population doubling of 20-24 h is found for Hepa-RP3. It is more rapid than with HEPARG® cells. A population doubling is seen in 24 h as early as day 2 following cell seeding. In addition Hepa-RP3 cells have changed their response to contact inhibition by showing increasing number of cells per surface unit at confluence.

2. Differentiation Status

Figure 9:
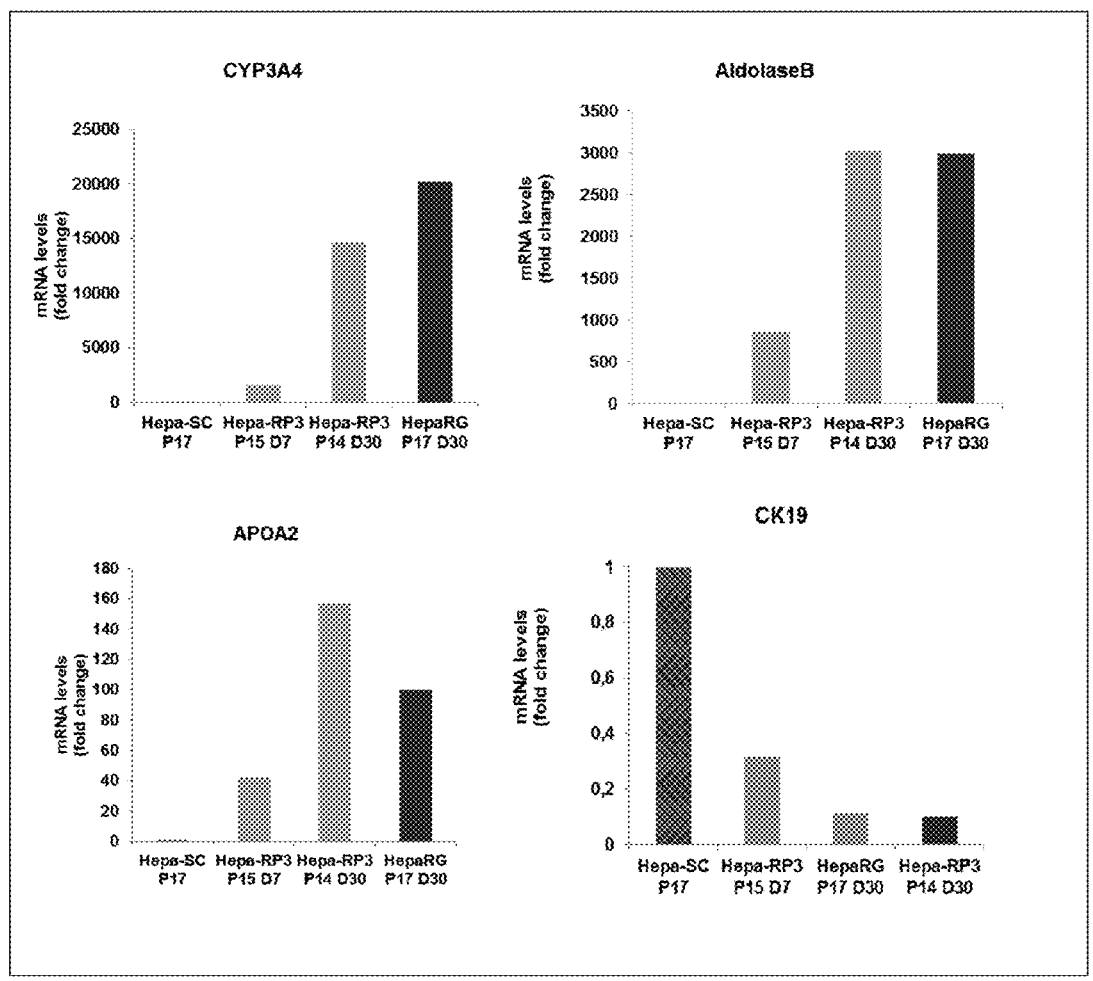
FIG. 9 shows graphs of the mRNA expression of three liver-specific markers and one progenitor marker in Hepa-RP3 and HEPARG® cells at the indicated passages.

The expression of 3 liver-specific functions have been analyzed at the mRNA level using RT PCR quantification: CYP3A4 (detoxification function), aldolase B (specific glycolytic function) and APOA1 (hepatic lipid metabolism). They are all highly expressed in Hepa-RP3, APOA1 being higher expressed than in Hear cells. A comparison has been performed with HEPARG® and Hepa-SC cells. As expected, these stem-like cells don't express liver markers. In contrast they express CK19, a cytokeratin weakly expressed in hepatocytes. The results are shown in FIG. 9.

3. Detoxification Function

Figure 10A:
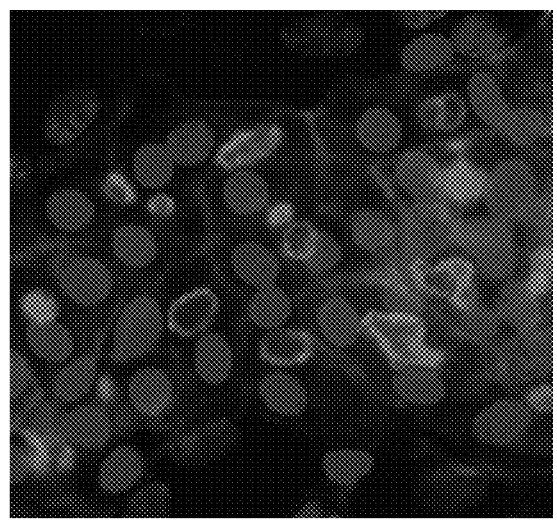
FIG. 10A shows F-actin deposition at the biliary poles of mature Hepa-RP3 cells.
Figure 10B:
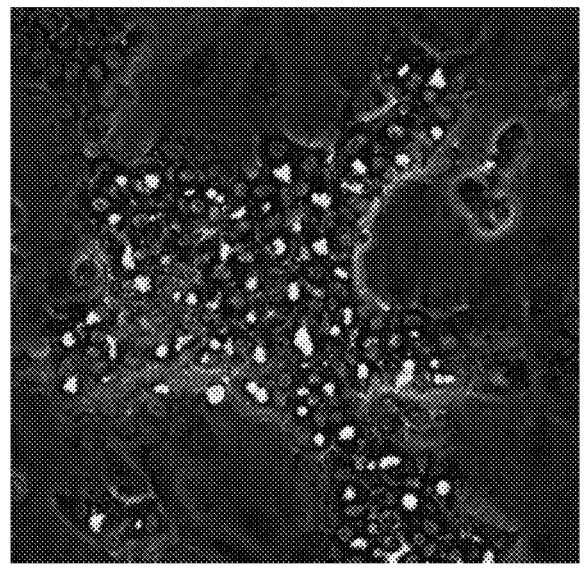
FIG. 10B shows MRP2 activity assay with fluorescent MRP2-substrate CDFA.

The Hepa-RP3 cells were analyzed for transporter activity and phase 1 enzymatic activities. FIGS. 10A-10B illustrate F-actin deposition at the biliary poles of mature Hepa-RP3 hepatocytes and MRP2 activity assay with the fluorescent MRP2-substrate (CDFA. Passage 33 (18 passages in Hydrocortisone-free medium)

Figure 11:
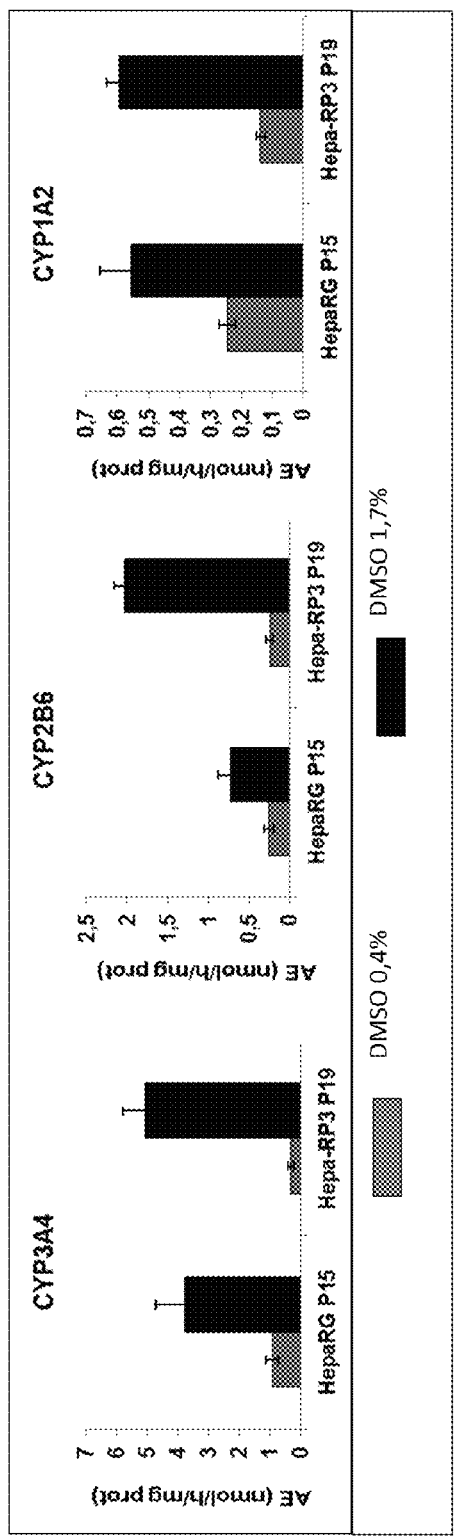
FIG. 11 shows graphs comparing three CYP450 enzyme activities for Hepa-RP3 and HEPARG®.

FIG. 11 shows comparison of three distinct CYP450 enzymes activity at indicated passages between the new Hepa-RP3 cell line and the parental HEPARG® measured using specific substrates. All the three were active in Hepa-RP3 cells and they are all induced by DMSO as in HEPARG® cells.

E. Cell Line Stability

Figure 12:
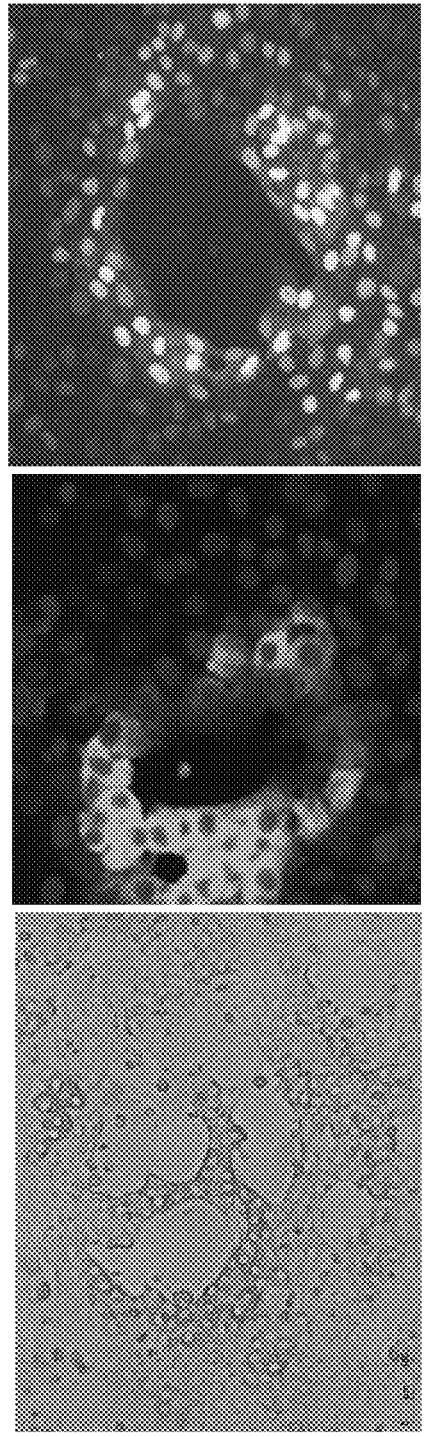
FIG. 12 shows images of cell line stability of the Hepa-RP3 cells, with the left panel showing a phase contrast micrograph of the cells at passage 19; the middle panel showing expression of transferrin; and the right panel showing expression of nuclear transcription factor HNF4 (light blue) and glutamine synthase (red), with the nuclei in dark blue.

The Hepa-RP3 cell line was tested for its ability to maintain the capacity to differentiate into hepatocytes and to keep the ratio between hepatocytes colonies and flat primitive biliary cells close to 50% for up to passage 20. Results are shown in FIG. 12. The left hand panel is a phase contrast micrograph of Hepa-RP3 at passage 19. The middle panel shows the expression of transferrin. The right hand panel shows expression of both nuclear transcription factor HNF4 (light blue) and glutamine synthase (red). The nuclei are shown in dark blue. As can be see, there is organization of a gradient of differentiation around an empty lumen. Cells keep the capacity to form colonies of mature hepatocytes. Increased richness in hepatocytes can be observed.

Finally, karyotyping stability has been analyzed through passages: Both chromosomic classification and CGH array of the complete genome analysis have been performed on passage 20. The whole genome appears well preserved.

Example 4

Figure 13:
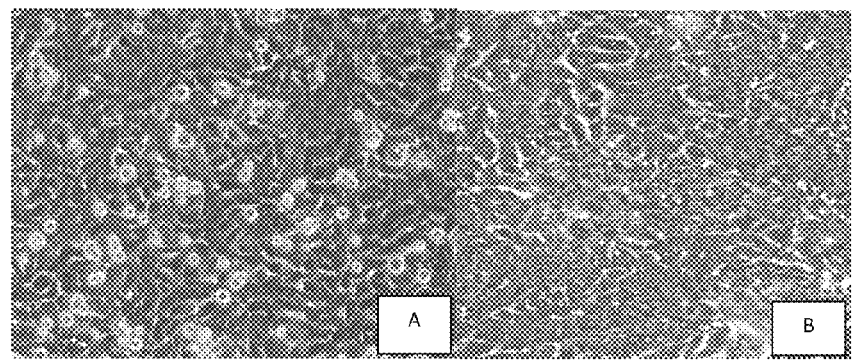
FIG. 13 shows phase contrast micrographs of Hepa-RP3 cells growing in corticoid-free proliferating medium at (A) passage 23 and (B) passage 33.

Use of Corticoid-Free Culture Conditions for Expanding Hepa-RP Cells: Functional Characteristics of the Cells when Undergoing Differentiation In this example, expansion and differentiation characteristics of the Hepa-RP3 cells were analyzed. In contrast to all previous examples described above, Hepa-RP cells were grown in the proliferating medium deprived of corticoid. As shown in FIG. 13, Hepa-RP3 cells growing in the proliferating medium deprived of hydrocortisone actively proliferate, but cannot commit to a differentiation program even when reaching confluence. The images shown are for passages 23 (A) and 33 (B). Notably, there was no significant change with number of passages.

Figure 14:
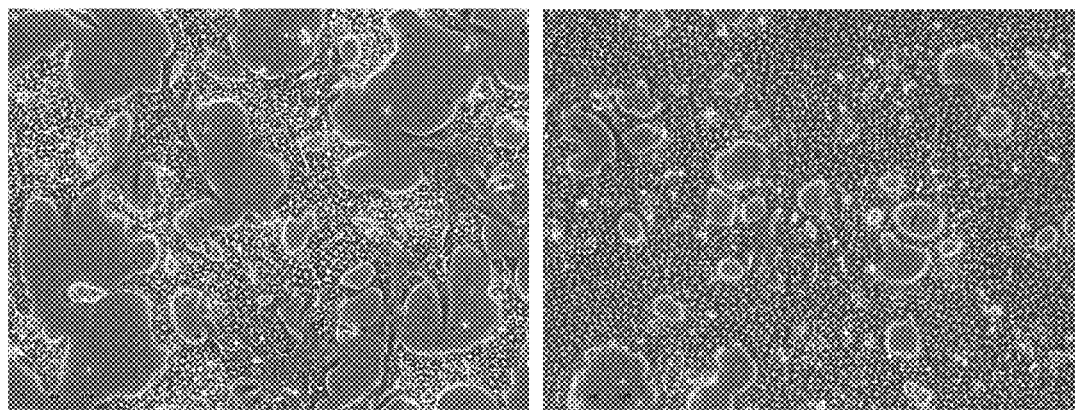
FIG. 14 shows two phase contrast micrographs of Hepa-RP3 colonies at passage 26.

Cells were expanded for long term in this corticoid-free medium, for instance 7 passages. Then, assays for getting commitment to differentiation were performed using the differentiation medium (containing 50 µM hydrocortisone plus 1% and then 1.5% DMSO as described above). FIG. 14 shows Hepa-RP3 hepatocyte colonies obtained at passage 26. We note i) the very efficient differentiation performed in most cells from the population; ii) the near complete disappearance of primitive biliary cells and the regular monolayer formed by hepatocytes (no piling up). In addition, in contrast to Hepa-RP cultured in conditions for obtaining cell behavior similar to HEPARG® (i.e. proliferating medium with corticoid), weak or no reversion of hepatocytes towards proliferating progenitors could be detected, so that differentiated hepatocyte colonies fell to fill the empty zones of the culture with undifferentiated progenitor cells, thus, strongly improving the stability of the culture.

Figure 15:
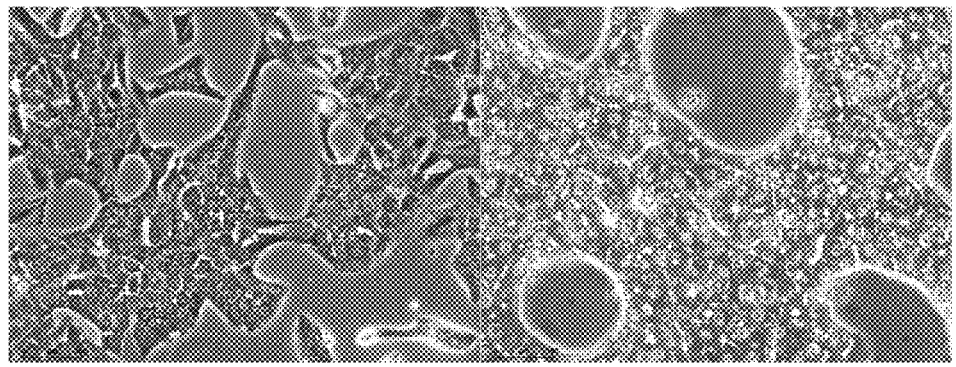
FIG. 15 shows images demonstrating the morphological characteristics of the Hepa-RP3 cells during differentiation.
Figure 16:
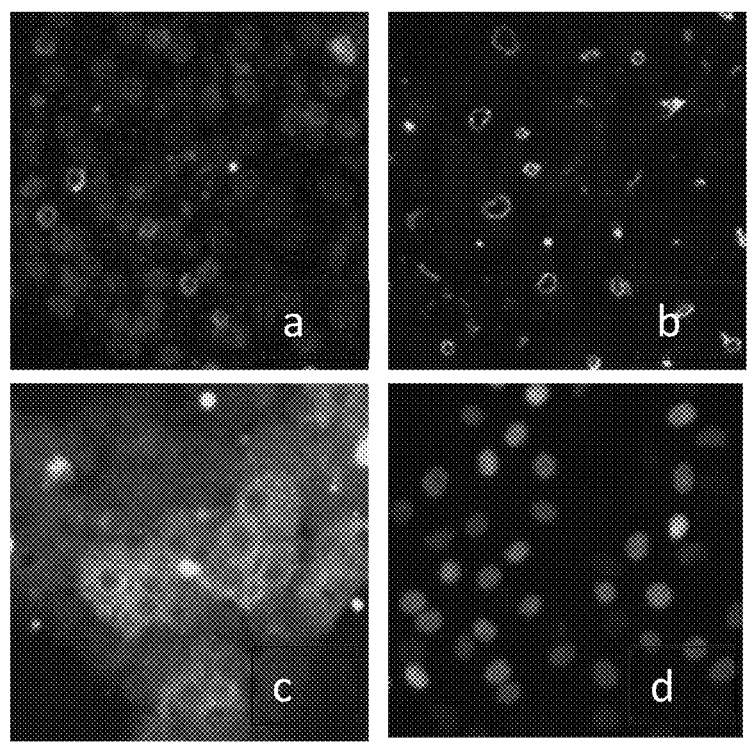
FIG. 16 shows images of Hepa-RP3 cells at passage 29 and immunolocalization of (A) pGP; (B) ZO-1; (C) CYP34; and (D) HNF4, which all characterize the high differentiation status of the cells.

As shown in FIG. 15, the morphological features are those of human primary hepatocytes and very similar to those obtained with HEPARG® cells. The panel on the left shows cells at passage 31, 4 days post-seeding in the differentiation medium (containing corticoid). The panel on the right shows cells at passage 31 and 12 days in presence of 1.5% DMSO. Note the numerous bile canalicular structures signing the high polarity of the cells. FIG. 16 shows differentiation markers of the Hepa-RP3 cells at passage 29, and specifically immunolocalization of a) pGP, a biliary polarized transporter, b) ZO-1, a biliary polarized junctional protein, c) CYP34 a hepatic specific CYP, and d) HNF4, a liver-specific transcription factor. These results demonstrate high differentiation status of the Hepa-RP3 cells.

Figure 17A:
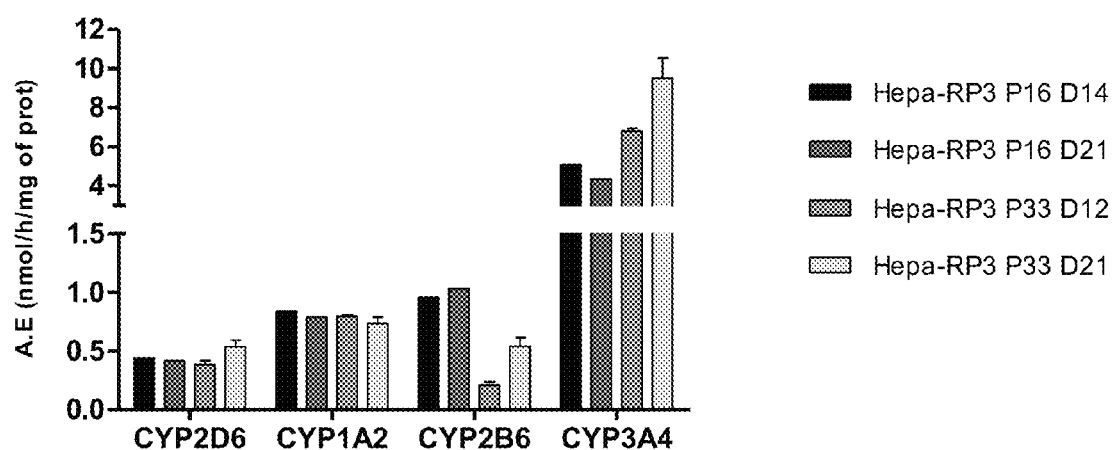
FIG. 17A shows a graph demonstrating the high stability of the Hepa-RP3 cell line; maintenance of the expression of main liver specific CYPs during 33 passages; comparison with their expression levels at passage 16.
Figure 17B:
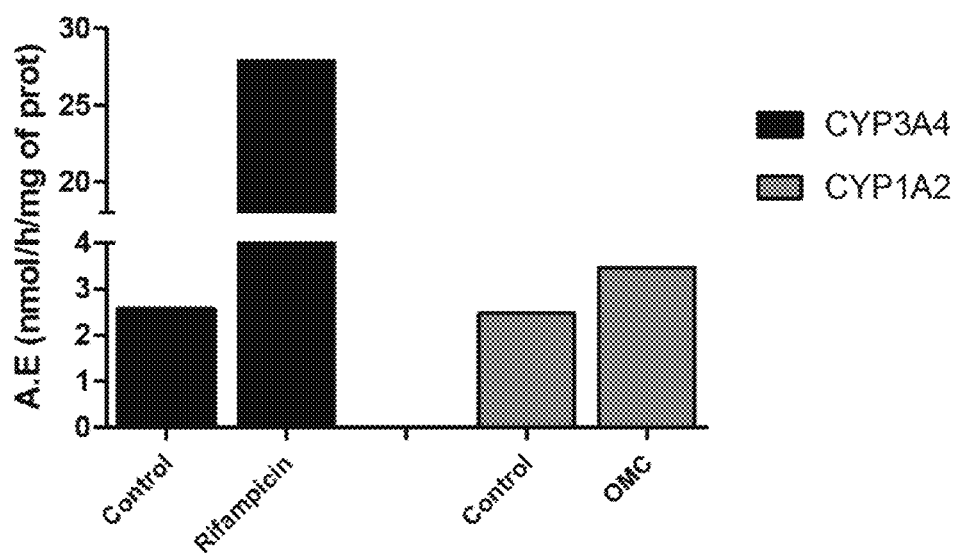
FIG. 17B shows a graph of the induction capacity of cytochromes CYP3A4 and CYP1A2 in Hepa-RP3 at passage 33.

Finally, four CYP enzymes were quantified for their activity at passage 33 (14 passages with expansion in condition of corticoid-free medium): CYP3A4, 1A2, 2B6, 2D6. All were functional and support activity close to that obtained at earlier passage (P16) suggesting high stability of the cell line (FIG. 17). It is also of great interest to observe the capacity of CYPs to respond to specific inducers, property very important for applications in toxicology.

Example 5

Applications for Stem-Like Cells Hepa-SCs and Hepa-RPs

Figure 18:
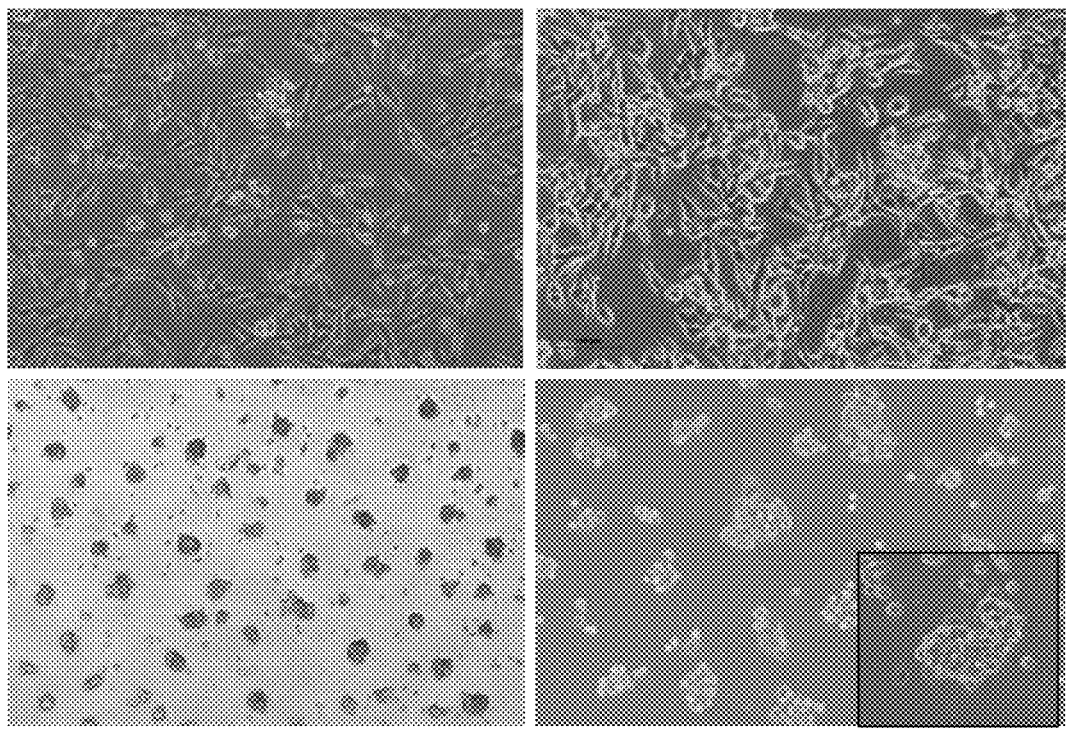
FIG. 18 shows images of spheroids of hepatic cells mixed with non-parenchymal cells.

The Hepa-SC cells were used to produce hepatic cell units: spheroids of bipotent hepatic cells. As shown in FIG. 18 spheroids of hepatic cells mixed with non-parenchymal cells including sinusoidal cells, stellate and kupffer cells were produced. An alternative to this approach could be the production of spheroids from progenitors submitted to shape constraint and mechano-transduction.

Figure 19:
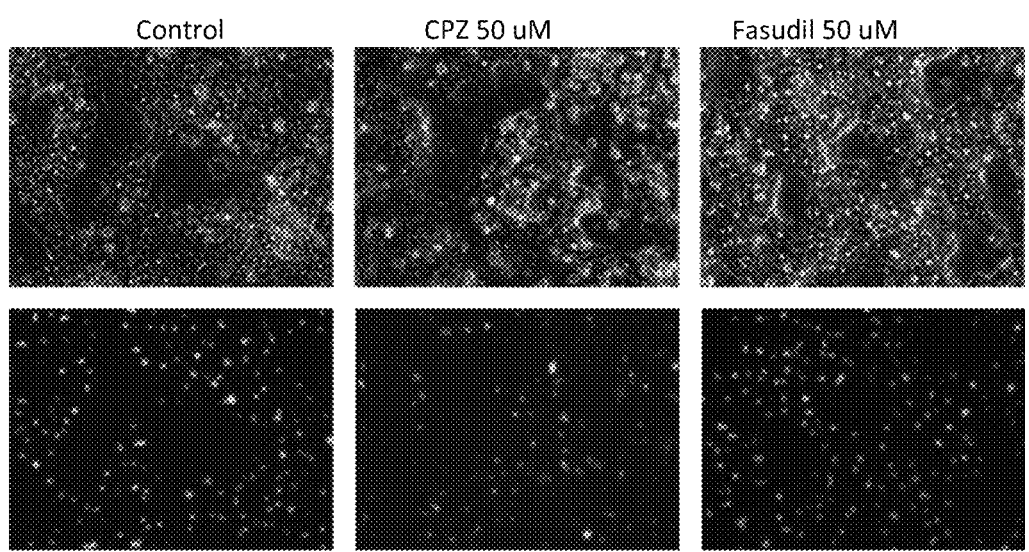
FIG. 19 shows images from using Hepa-RP3 cells to screen for cholestatic drugs chlorpromazine (CPZ) and fasudil.

Hepa-RPs could be used for screening cholestatic drugs. As shown in FIG. 19, evidence of two opposite cholestatic effects (Chlorpromazine CPZ and Fasudil) was seen on the bile saccular canaliculi in Hepa-RP at passage 29 (10 passages with a corticoid-free medium). Alterations (constriction and dilatation) associated with delay in MRP2 transport of CDFDA compared to control cells were seen. These morphological and functional changes will constitute part of a cholestatic test aiming at screening drugs susceptible to induce adverse cholestatic disease.

Hepa-RP cells could also be used for screening genotoxic compounds. Conditions allowing the production of pure populations of hepatocytes (e.g., cultures consisting essentially of hepatocytes and being essentially free of biliary cells) using corticoid-free proliferating medium will be very convenient. Until now no efficient and appropriate hepatic model was reported to be suitable for setting a genotoxicity test onto liver cells.

Example 6

Differentiation Programming of Hepa-SC Cells to Non-Hepatic Cell Lines

Figure 20:
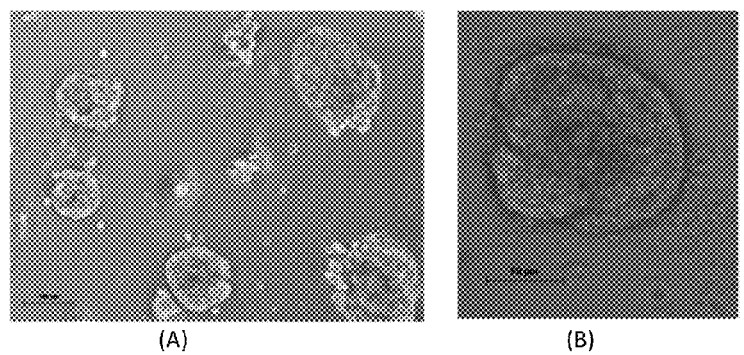
FIG. 20 shows (A) a phase contrast micrograph and (B) magnified view of beta-pancreatic islet spheroids reprogrammed from Hepa-SC cells after 15 days of culture in thick matrigel.

In this Example, Hepa-SC cells were differentiated into beta-pancreatic cells using retinoic acid is the morphogen factor. Hepa-SC cells were seeded at very high density ($8 \times 10^5$) in the medium used for their propagation except the epigenetic factor (5-azacytidine) which was excluded. The cells were detached by trypsin and seeded at $4 \times 10^5$ onto thick soft matrigel in order to get spheroids, as shown in FIG. 20. Retinoic acid was added to the medium used for cell maintenance (example LT medium) often enriched with various other growth factor. This morphogen signal is limited to 24 hours. Then the cells were cultured in the same medium without retinoic acid.

Figure 21:
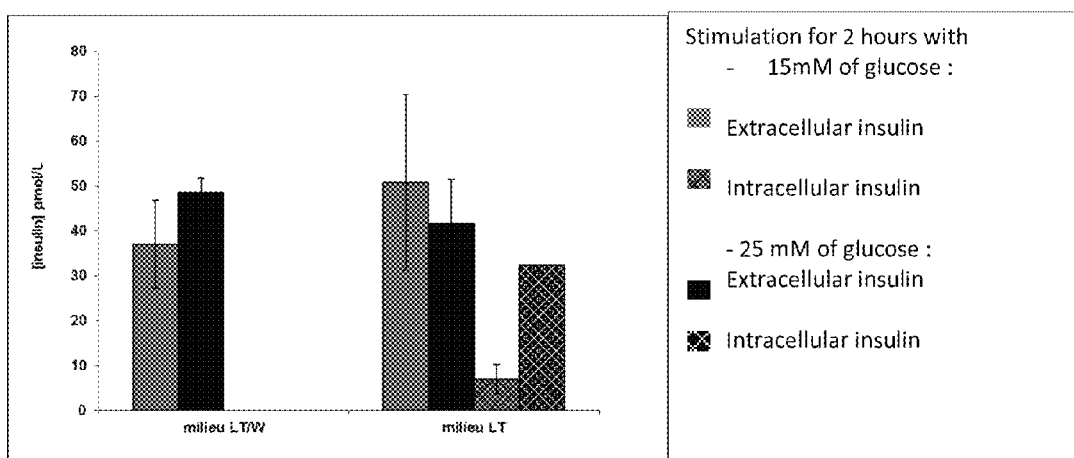
FIG. 21 shows a graph of insulin production of the beta-pancreatic cells.

Beta-pancreatic cells, designated as beta-RP cells, were obtained and maintained in conditions allowing them to organize 3D structures or spheroids within few hours (12-15 h). These spheroids mimic beta-pancreatic islets. FIG. 20 shows phase contrast micrographs of beta-pancreatic islets obtained from Hepa-SCs seeded onto soft matrigel and observed after 15 days of culture. Note the cell organization observed at high magnification (B). They can be distributed in wells or in frozen vials. An alternative with another soft hydrogel (alginate, gelatin, etc.) is envisioned. In addition, the beta-RP cells include the different types of cells responsible of insulin, glucagon, and α-amylase secretion. Thus, they are positive for insulin secretion, as shown in FIG. 21. They remain alive for several weeks (for instance, 6 weeks) when maintained in conditions of soft hydrogel such as thick matrigel and in the LT medium (Zanini C. 2012) or LT in combination with William's E medium (v/v).

Figure 22:
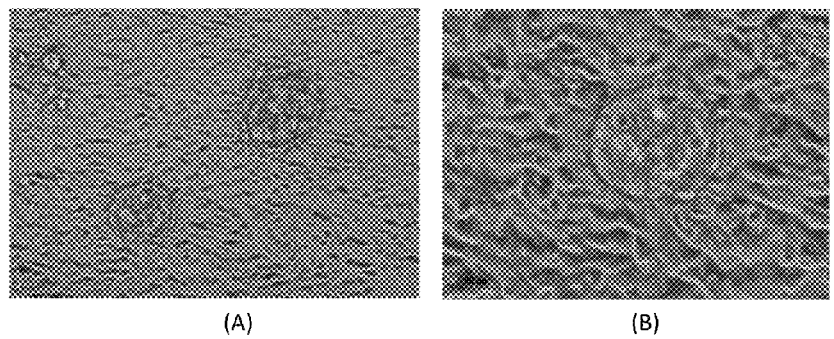
FIG. 22 shows (A) a phase contrast micrograph and (B) magnified view of beta-pancreatic islets that spontaneously formed in a monolayer of confluent Hepa-SC cells.

An alternative system for producing beta-RP cells was developed using the same protocol as described above, except that the cells were seeded at $4 \times 10^5$ onto a stiff surface such as plastic coated in matrigel, in order to put the cells in conditions of cell proliferation, meaning that a cell line can be established with the cell line established from Hepa-SC and directed to pancreatic lineage as beta-RP cells, but maintained in monolayer on a stiff support made of polycarbonate plastic covered by thick layer of matrigel. In that conditions cells attach, spread and divide slowly. At confluence, they can form spheroids distributed throughout the monolayer. FIG. 22 shows phase contrast micrographs of beta-pancreatic islets spontaneously formed in a monolayer of confluent Hepa-SC cells growing onto thick matrigel (A). Note the cell organization observed at high magnification (B).

A variation that could be used in either system is a mixed medium of LT/William's E. It permits production of an increased number of spheroids and an increased proliferation activity of the cell line. Addition of low concentration of matrigel in suspension into the culture medium improves the long term stability of the cells on both systems.

We postulate that Hepa-SC cells can redifferentiate into intestine cells, mainly enterocytes, in, presence of specific drivers of this differentiation pathway. Growth factors such as bFGF and mainly the R-spondin which specifically binds to the Leucine-rich repeat-containing G protein-coupled receptors 4-6 (LGR4-LGR6) should play a role in the commitment to differentiation (Sato T et al., 2009). R-spondin is also one of the potent Wnt agonists that exert profound trophic effects on Wnt-driven stem cells compartments (Peng W C et al., 2013) while Rho-kinase inhibitor, y27632 improve cell recovery. In addition, GSK3-3 inhibitor such as CHIR 99021 and the MEK/ERK inhibitor PD98059 are then, used sequentially. The same protocol as for beta-pancreatic cells will be used: after the shape-constraint signal for 20 hours Hepa-SC cells will be detached and suspended in a medium containing the cocktail of factors described above and then, distributed to wells coated or not with thick soft matrigel.

Likewise, for directing Hepa-SC cells toward osteoblasts, the same mechano-transduction signaling protocol is used: Hepa-SC cells are submitted to the shape-constraint signal for 20 hours, then detached and re-seeded in a medium containing the specific morphogen factors. This medium is composed of DMEM high glucose+10% FCS+dexamethasone 10-7M, 25 µg/ml ascorbic acid. The cells grow and reach confluence. After 14 days they have undergone differentiation including production of extracellular fibers on which calcium concretion will deposit.

What is claimed:

1. A method of directing differentiation of a stem-like cell line designated as Hepa-SC cells, deposited at the Collection Nationale de Cultures de Microorganismes, Institut Pasteur, under Deposit No. CNCM I-4980, into a target population of reprogrammed cells, said method comprising:
    culturing said Hepa-SC cells under conditions of mechanical stress and in the presence of at least one differentiation factor for said target cell population for a time period sufficient for the Hepa-SC cells to commit to differentiation;
    transferring said committed cells to a culture medium comprising said differentiation factor; and
    maintaining said cells in culture without said mechanical stress to yield said reprogrammed cells;
    wherein said culturing said Hepa-SC cells under conditions of mechanical stress comprises plating said Hepa-SC cells at high density sufficient to provide shape constraint on said Hepa-SC cells;
    wherein said differentiation factor is selected from the group consisting of cortico-steroids, DMSO, retinoic acid, o-estrogens, thyroid hormones, synthetic analogues thereof, and combinations thereof.

2. The method of claim 1, wherein said reprogrammed cells are progenitor cells having bipotent properties to differentiate into hepatocyte and biliary cell lineages.

3. The method of claim 2, further comprising culturing said progenitor cells in culture medium comprising at least one cortico-steroid and DMSO.

4. The method of claim 2, further comprising culturing said progenitor cells in culture medium that is essentially free of cortico-steroid and/or DMSO.

5. The method of claim 4, further comprising passaging said progenitor cells in said culture medium that is essentially free of cortico-steroid and/or DMSO more than 18 passages.

6. The method of claim 5, further comprising directing said passaged progenitor cells to differentiate into hepatocytes by culturing said passaged progenitor cells in culture medium comprising at least one cortico-steroid and DMSO in a quantity sufficient to induce differentiation.

7. The method of claim 4, further comprising maintaining said progenitor cells in said culture medium, and subsequently directing said progenitor cells to differentiate into hepatocytes by culturing said passaged progenitor cells in culture medium comprising at least one cortico-steroid and DMSO in a quantity sufficient to induce differentiation at any passage up to passage 18 or more.

8. The method of claim 1, wherein said target population of cells are non-hepatic cells selected from the group consisting of beta-pancreatic cells, enterocytes, and osteoblasts.

* * * * *